United States Patent
Petersen et al.

(12)

(10) Patent No.: US 6,288,081 B1
(45) Date of Patent: Sep. 11, 2001

(54) **USE OF 7-(1-AMINOMETHYL-2-OXA-7-AZA-BICYCLO[3.3.0]OCT-7-YL)-QUINOLONE CARBOXYLIC ACID AND NAPHTHYRIDONE CARBOXYLIC ACID DERIVATIVES FOR TREATING *HELICOBACTER PYLORI* INFECTIONS AND THE GASTRODUODENAL DISEASES ASSOCIATED THEREWITH**

(75) Inventors: Uwe Petersen, Leverkusen; Michael Matzke, Wuppertal; Thomas Jaetsch, Köln; Thomas Schenke, Bergisch Gladbach; Thomas Himmler, Odenthal; Stephan Bartel, Kürten; Bernd Baasner, Bergisch Gladbach; Hans-Otto Werling, Wuppertal; Klaus Schaller, Wuppertal; Harald Labischinski, Wuppertal; Rainer Endermann, Wuppertal, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/319,848

(22) PCT Filed: Dec. 3, 1997

(86) PCT No.: PCT/EP97/06751

§ 371 Date: Aug. 6, 1999

§ 102(e) Date: Aug. 6, 1999

(87) PCT Pub. No.: WO98/26768

PCT Pub. Date: Jun. 25, 1998

(30) Foreign Application Priority Data

Dec. 16, 1996 (DE) ............................................. 196 52 219

(51) Int. Cl.[7] ................ A61K 31/4709; A61K 31/4375; C07D 215/56; C07D 471/04; A61D 1/04
(52) U.S. Cl. .................... 514/312; 514/229.2; 514/230.2; 514/291; 514/292; 514/293; 514/300; 544/66; 544/101; 546/80; 546/81; 546/83; 546/84; 546/123; 546/156; 548/453
(58) Field of Search .................................... 546/156, 123, 546/80, 81, 83, 84; 544/101, 66; 548/453; 514/312, 300, 229.2, 230.2, 291, 292, 293

(56) References Cited

U.S. PATENT DOCUMENTS

| | | | | |
|---|---|---|---|---|
| 5,395,944 | * | 3/1995 | Petersen | 548/453 |
| 5,574,161 | * | 11/1996 | Petersen | 546/167 |
| 5,578,604 | * | 11/1996 | Himmler | 514/312 |

FOREIGN PATENT DOCUMENTS

| | | |
|---|---|---|
| 0 589 318 A | 3/1994 | (EP). |
| 0 671 391 A | 9/1995 | (EP). |
| WO 97 31919 A | 9/1997 | (WO). |

OTHER PUBLICATIONS

A Small Animal Model of Human Helicobacter pylori Active Chronic Gastritis, Gastroenterology 1990;99:1315–1323; 1990 by the American Gastroenterological Association 0016–5085/90 (Adrian Lee, et al).

NIH Consensus Statement, vol. 12, No. 1, Feb. 7–9, 1994; 12(1): 1–22; Helicobacter Pylori in Peptic Ulcer Disease, National Institutes of Health, Office of the Director.

Susceptibility of Campylobacter pylori to macrolides and fluoroquinolones, Journal of Antimicrobial Chemotherapy (1988) 22, 631–636 (Dwight J. Hardy, et al).

Comparative In Vitro Activities of Six New Fluoroquinolones and Other Oral Antimicrobial Agents against Campylobacter pylori; Antimicrobial Agents and Chemotherapy, Jan. 1989, p. 108–109;0066–4804/89/010108–02, vol. 33, No. 1; Copyright 1989, American Society for Microbiology; (Andrew E. Simor, et al).

* cited by examiner

*Primary Examiner*—Evelyn Mei Huang
(74) *Attorney, Agent, or Firm*—Norris McLaughlin & Marcus

(57) ABSTRACT

The invention relates to the use of quinolone- and naphthyridonecarboxylic acid derivatives which are substituted in position 7 by a 1-aminomethyl-2-oxa-7-azabicyclo[3.3.0] oct-7-yl radical, and of their salts for the therapy of *Helicobacter pylori* infections and associated gastroduodenal disorders.

8 Claims, No Drawings

USE OF 7-(1-AMINOMETHYL-2-OXA-7-AZA-BICYCLO[3.3.0]OCT-7-YL)-QUINOLONE CARBOXYLIC ACID AND NAPHTHYRIDONE CARBOXYLIC ACID DERIVATIVES FOR TREATING *HELICOBACTER PYLORI* INFECTIONS AND THE GASTRODUODENAL DISEASES ASSOCIATED THEREWITH

This application is a 371 of PCT/EP97/06751 filed on Dec. 3, 1997.

The invention relates to the use of quinolone- and naphthyridonecarboxylic acid derivatives which are substituted in position 7 by a 1-aminomethyl-2-oxa-7-aza-bicyclo[3.3.0]oct-7-yl radical, and of their salts for the therapy of *Helicobacter pylori* infections and associated gastroduodenal disorders.

In the years following the rediscovery of *Helicobacter pylori* (*H. pylori*; old name *Campylo-bacter pylori*) by Warren and Marshall in 1983, the pathophysiological ideas on the genesis of gastro-duodenal disorders in man were developed further in a fundamental way.

*H. pylori* is considered to be the cause of type B gastritis and seems to play a causative part in the perpetuation of peptic ulcers. Epidemiological and pathological investigations likewise indicate a connection between the long-term colonization of the mucosa of the stomach by the bacterium and the formation of certain forms of stomach carcinoma. Because of this, *H. pylori* was, in 1994, classed as a carcinogen of the first order (most dangerous cancer-causing category). A rare form of stomach cancer, MALT lymphoma (mucosa-associated lymphoid tissue) appears likewise frequently to be caused by the germ. Indeed, in initial casuistries, after *H. pylori* eradication, not only the reactive infiltrates disappeared, but even some of the MALT lymphomas of low malignancy. A connection with Ménétrier's syndrome is also being discussed. The role of *H. pylori* in functional gastropathy (nonulcerous dyspepsia) is still unclear.

Various epidemiological studies reach the conclusion that approximately half of the population of the world is infected with the bacterium. The likelihood of colonization of the stomach by Helicobacter increases as a function of age. The optimum adaptation of Helicobacter to the living conditions in the unusual, low-competition habitat of the stomach seems to be the precondition for successful establishment of the chronic infection and for the wide distribution of this pathogenic species.

The pathogens are, with their flagella, not only highly mobile in liquid media but also in the viscous mucous of the mucosa of the stomach, they adhere to the epithelial cells of the stomach and they multiply best at an oxygen content of 5%, as is prevalent in the mucous of the stomach wall. Moreover, the bacteria produce large amounts of the enzyme urease which cleaves urea into ammonia and carbon dioxide. The "cloud of ammonia" which is formed possibly assists the bacteria in neutralizing the acidic medium in the microenvironment, resulting in protection against the aggressive stomach acid.

Peptic Ulcers

The introduction of the histamine $H_2$-receptor antagonists in the 1970s was a milestone in the therapy of peptic ulcers. World-wide, the frequency of surgical interventions for the treatment of the ulcer decreased dramatically. This principle of the acid blockade was improved even more by the development of the more strongly effective proton pump inhibitors.

However, the antacid therapy has a causal effect—i.e. by disinfectant treatment—only on the symptoms of the ulcer, not on the natural cause of the disease which is characterized by the occurrence of relapses. This is because virtually all ulcus duodeni patients and a predominant majority of the patients suffering from ulcus ventriculi have an *H. pylori* infection of the stomach and therefore suffer from infectious diseases. Only ulcerations caused by nonsteroidal antiphlogistics are not associated with an *H. pylori* infection.

Thus, according to the recommendations of a consensus conference which was organized by the American National Institute of Health (NIH) in 1994, all patients suffering from peptic ulcers should, in the case of a positive germ test, undergo eradication therapy directed against *H. pylori* (NIH Consensus Statement 1: 1–23; 1994). The arguments in favour of this came from controlled therapy studies which showed that, after successful germ eradication, the ulcer relapse rates decrease dramatically (0%–29% versus 61%–95%).

*H. pylon* Therapy

In practice, the current eradication of *H. pylori* is not particularly simple. There is no simple and nevertheless reliably effective therapy. The germ is located under the layer of mucous, where it is well protected and difficult to attack.

In vitro, *H. pylori* shows sensitivity towards numerous antibiotics. However, these antibiotics are, as a monotherapy, not effective in vivo. They include, inter alia, penicillin, amoxicillin, tetracycline, erythromycin, ciprofloxacin, metronidazole and clarithromycin. Likewise, bismuth salts and to a lesser extent even proton pump inhibitors (omeprazole, lansoprazole) have antibacterial activity in vitro, but not in vivo.

Among all the therapy modalities used hitherto for eradicating *H. pylori*, to date only the triple therapies below are sufficiently effective:

1. classic bismuth triple therapy (bismuth salt plus two antibiotics) and
2. modified triple therapy (antacid plus two antibiotics).

However, these regimes are complicated eradication methods with poor compliance which may in up to 35% of all cases be associated with side effects (stomach aches, sickness, diarrhoea, a dry mouth, impairment of taste and allergic skin reactions, etc.). This makes a broader use more difficult. Another great disadvantage is the large number of medicaments which have to be taken every day (12–16 tablets/day). This is particularly pronounced in the quadruple therapy where an acid secretion inhibitor is administered simultaneously with the classic triple therapy.

However, the dual therapy (combination of amoxicillin with omeprazole), which is better tolerated and is propagated in Germany, has only a low efficacy and even seems to fail substantially in the case of patients who have been pre-treated with omeprazole and in the case of smokers.

The antibiotic components which are generally administered in triple therapies are amoxicillin, nitroimidazole compounds (metronidazole, tinidazole), tetracycline and, more recently, macrolides (clarithromycin) [in 3–4 partial doses].

Throughout the world, eradication rates of 70–90% are achieved. However, this eradication success can be influenced by a variety of factors:

1. Primarily, mention has to be made of the resistance of the germ (developing countries: up to 60%, Germany: up to 10%) towards metronidazole, the antibiotic which is most frequently used in the triple therapy. In the treatment with Clarithromycin, reference is likewise made to the disadvantage of a resistance development of up to 10%.

2. Another factor which has to be mentioned is the abovementioned compliance of the patients.

Animal Model

An *H. felis* mouse model has been described as a suitable animal model [A. Lee et al., Gastroentrology 99: 1315–1323 (1990)] and we modified this model in such a way that it is highly suitable for the screening and the comparative assessment of the abovementioned compounds.

In spite of considerable morphological differences, the corkscrew-like, urease-forming bacterium *H. felis* is very closely related to *H. pylori*. *H. felis* is a natural inhabitant of the mucosa of the stomach of dogs and cats. After oral inoculation, the pathogens also colonize the stomach of mice, in a similar manner to that in which *H. pylori* colonizes the stomach of humans. The established chronic long-term infection leads to active gastritis in germ-free mice and induces a corresponding immune response.

The therapeutic efficacy of test samples determined in the *H. felis* mouse model is considered to be very predictive for the corresponding clinical activity.

In spite of very good in vitro activity of antibiotics (for example Amoxicillin or erythromycin) against *H. pylori*, these do not show any significant clinical therapeutic effect after having been administered in monotherapy. This fact is also represented by the *H. felis* mouse model. Correspondingly, the clinically accepted eradicative effect of the classic triple therapy could also be confirmed in the *H. felis* mouse model.

Antibacterially effective 7-(1-aminomethyl-2-oxa-7-aza-bicyclo[3.3.0]oct-7-yl)quinolone- and -naphthyridonecarboxylic acid derivatives have already been disclosed in European Patent Application 589 318 (Bayer). The surprising activity of such compounds for controlling Helicobacter spp. has hitherto not been disclosed. Furthermore, European Patent Application 671 391 (Bayer) discloses that 7-(1-aminomethyl-2-oxa-7-aza-bicyclo[3.3.0]oct-7-yl)-1-cyclopropyl-6,8-difluoro-1,4-dihydro-4-oxo-5-vinyl-3-quinolonecarboxylic acid is likewise effective against *H. pylori*. However, this activity is relatively low. The 5-ethinyl derivative, which is also described in this application, has been found to be unstable and therefore unsuitable for therapeutic use. Japanese Patent Application JP 8048629 (Dainippon) discloses that compounds such as 8-chloro-1-cyclopropyl-7-([S,S]-2,8-diazabicyclo[4.3.0]non-8-yl)-6-fluoro-1,4-dihydro-4-oxo-3-quinolinecarboxylic acid (BAY Y 3118) have antibacterial activity against *H. pylori*. It is also known that a number of highly active quinolones, such as, for example, ciprofloxacin, lomefloxacin or ofloxacin (Journal of Antimicrobial Chemotherapy 22, 631–636 [1988], Antimicrobial Agents and Chemotherapy, 33, 108–109 [1989]), exhibit in vitro activity against Helicobacter spp. in the animal model (*H. felis*, mouse), however, it was found that these clinically used, antibacterially active quinolones are not capable of eradicating the germ. It is also not possible to achieve eradication of *H. felis* in the mouse model by monotherapeutic treatment with highly active quinolones which have hitherto not been introduced into the market, such as, for example, with the abovementioned BAY Y 3118. The use of trovafloxacin or its derivatives in combination with other antibiotics, such as amoxicillin or tetracyclines, or proton pump inhibitors, such as Omeprazole, for the therapy of *H. pylori* is described in the Patent Applications EP 676 199 and GB 2 289 674 (Pfizer). It was an object of the present invention to provide well-tolerated active compounds which are capable of eradicating this highly specialized bacterium by simple monotherapy.

It has now been found that the compounds of the formula (I)

$$T-Q \qquad (I),$$

in which

Q represents a radical of the formulae

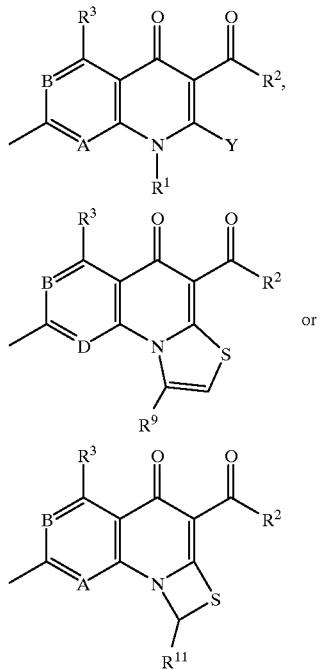

in which $R^1$ represents alkyl having 1 to 4 carbon atoms which is optionally mono- to trisubstituted by halogen or hydroxyl, alkenyl having 2 to 4 carbon atoms, cycloalkyl having 3 to 6 carbon atoms which is optionally substituted by 1 or 2 fluorine atoms, bicyclo[1.1.1]pent-1-yl, 1,1-dimethylpropargyl, 3-oxetanyl, methoxy, amino, methylamino, dimethylamino, phenyl which is optionally mono- or disubstituted by halogen, amino or hydroxyl, isoxazolyl, thiadiazolyl, $R^2$ represents hydroxyl, alkoxy having 1 to 4 carbon atoms which is optionally substituted by hydroxyl, methoxy, amino, dimethylamino or ethoxycarbonyl, benzyloxy, allyloxy, propargyloxy or (5-methyl-2-oxo-1,3-dioxol-4-yl)-methyloxy, acetoxymethyloxy, pivaloyloxymethyloxy, 5-indanyloxy, phthalidinyloxy, 3-acetoxy-2-oxobutyloxy, nitromethyl or dialkoxycarbonylmethyl having 1 to 2 carbon atoms in each alkyl moiety, $R^3$ represents hydrogen, amino, hydroxyl, methyl or halogen, $R^9$ represents hydrogen or optionally methoxy-, hydroxyl- or halogen-substituted alkyl having 1 to 3 carbon atoms, $R^{11}$ represents hydrogen, $CH_3$ or $CH_2F$, A represents N or C—$R^7$ in which $R^7$ represents hydrogen, halogen, $CF_3$, $OCH_3$, $OCHF_2$, $CH_3$, CN, CH=$CH_2$ or C≡CH or else together with $R^1$ may form a bridge of the structure —*O—$CH_2$—CH—$CH_3$, —*S—$CH_2$—$CH_2$—, —*S—$CH_2$—CH—$CH_3$, —*$CH_2$—$CH_2$—CH—$CH_3$ or —*O—

CH$_2$—N—R$^8$ where the atom marked with * is attached to the carbon atom of A and in which R$^8$ represents hydrogen, methyl or formyl, B represents N, C—H, C—F, C—Cl, C—NO$_2$, C—NH$_2$, D represents N or C—R$^{10}$ in which
R$^{10}$ represents hydrogen, halogen, CF$_3$, OCH$_3$, OCHF$_2$ or CH$_3$ or else together with R$^9$ may form a bridge of the structure —*O—CH$_2$—, —*NH—CH$_2$—, —*N(CH$_3$)—CH$_2$—, —*N(C$_2$H$_5$)—CH$_2$—, —*N(c—C$_3$H$_5$)—CH$_2$—or —*S—CH$_2$— where the atom marked with * is attached to the carbon atom of D, Y represents hydrogen or together with R$^2$ may form a bridge of the structure —*S—NH— where the atom marked with * represents Y, and T represents a radical of the formula

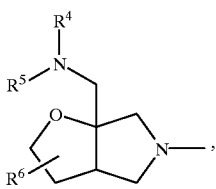

in which
R$^4$ represents H, CH$_3$, C$_2$H$_5$, optionally amino-substituted acyl having 1 to 5 carbon atoms, alkoxycarbonyl, aminocarbonyl, alkylthiothiocarbonyl and dialkoxyphosphoryl having 1 to 4 carbon atoms in the alkyl moiety,
R$^5$ represents H, CH$_3$, C$_2$H$_5$ and
R$^6$ represents H, CH$_3$, and their pharmaceutically useful hydrates and acid addition salts and the alkali metal, alkaline earth metal, silver and guanidinium salts of the parent carboxylic acids have high antibacterial activity against Helicobacter spp. and can be employed for eradicating this pathogen.

Preference is given to the compounds of the formula (I) in which
Q represents a radical of the formula

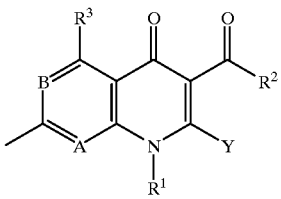

in which
R$^1$ represents alkyl having 1 to 4 carbon atoms which is optionally mono- to trisubstituted by fluorine, represents vinyl, optionally fluorine-substituted cyclopropyl, bicyclo[1.1.1]pent-1-yl, 1,1-dimethylpropargyl, 3-oxetanyl, methylamino, phenyl which is optionally mono- or disubstituted by fluorine, amino or hydroxyl, thiadiazolyl,
R$^2$ represents hydroxyl, optionally ethoxycarbonyl-substituted alkoxy having 1 to 4 carbon atoms, benzyloxy, allyloxy, propargyloxy,
R$^3$ represents hydrogen, amino, hydroxyl, methyl or fluorine,
A represents N or C—R$^7$ in which R$^7$ represents hydrogen, halogen, CF$_3$, OCH$_3$, OCHF$_2$, CH$_3$, CN, CH═CH$_2$ or C≡CH or else together with R$^1$ may form a bridge of the structure —*O—CH$_2$—CH—CH$_3$ or —*O—CH$_2$—N—R$^8$ where the atom marked with * is attached to the carbon atom of A and in which R$^8$ is hydrogen or methyl, B represents N, C—H, C—F, C—Cl, C—NH$_2$, Y represents hydrogen or together with R$^2$ may form a bridge of the structure —*S—NH— where the atom marked with * represents Y, and T represents a radical of the formula

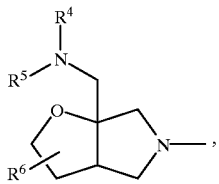

in which
R$^4$ represents H, CH$_3$, C$_2$H$_5$, optionally amino-substituted acyl having 1 to 5 carbon atoms, alkoxycarbonyl, aminocarbonyl, alkylthiothiocarbonyl and dialkoxyphosphoryl having 1 to 4 carbon atoms in the alkyl moiety,
R$^5$ represents H, CH$_3$, C$_2$H$_5$ and
R$^6$ represents H, and their pharmaceutically useful hydrates and acid addition salts and to the alkali metal, alkaline earth metal, silver and guanidinium salts of the parent carboxylic acids.

Particular preference is given to the compounds of the formula (I) in which
Q represents a radical of the formula

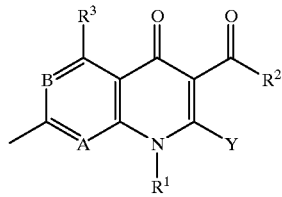

in which
R$^1$ represents alkyl having 1 to 4 carbon atoms which is optionally mono- or disubstituted by fluorine, optionally fluorine-substituted cyclopropyl, phenyl which is optionally mono- or disubstituted by fluorine,
R$^2$ represents hydroxyl, optionally ethoxycarbonyl-substituted alkoxy having 1 to 4 carbon atoms, benzyloxy, allyloxy, propargyloxy,
R$^3$ represents hydrogen, amino, hydroxyl, methyl or fluorine,
A represents N or C—R$^7$ in which
R$^7$ represents hydrogen, chlorine, fluorine, OCH$_3$, OCHF$_2$, CH$_3$ or CN or else together with R$^1$ may form a bridge of the structure —*O—CH$_2$—CH—CH$_3$, or —*O—CH$_2$—N—CH$_3$ where the atom marked with * is attached to the carbon atom of A,
B represents N, C—H, C—F,
Y represents hydrogen or together with R$^2$ may form a bridge of the structure —*S—NH— where the atom marked with * represents Y, and T represents a radical of the formula

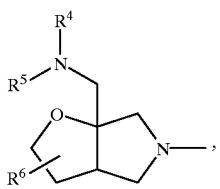

in which
R⁴ represents H, CH$_3$, C$_2$H$_5$, optionally amino-substituted acyl having 1 to 4 carbon atoms or alkoxycarbonyl having 1 to 4 carbon atoms in the alkyl moiety,
R⁵ represents H and
R⁶ represents H, and their pharmaceutically useful hydrates and acid addition salts and the alkali metal, alkaline earth metal, silver and guanidinium salts of the parent carboxylic acids.

Most of the compounds which are suitable for the use according to the invention have already been disclosed in European Patent Application 589 318, or they can be prepared by the processes described therein. Thus, the compounds of the formula (I) are obtained, for example, by reacting a bicyclic amine T—H with a quinolone skeleton Q-Hal, where Hal represents, for example, a halogen atom as leaving group, in accordance with the equation below:

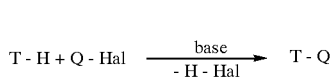

(I)

The 7-halogeno-quinolonecarboxylic acid derivatives Q-Hal used for preparing the compounds of the formula (I) according to the invention are known, or they can be prepared by known methods. Thus, the 7-chloro-8-cyano-1-cyclopropyl-6-fluoro-1,4-dihydro-4-oxo-3-quinolinecarboxylic acid or ethyl 7-chloro-8-cyano-1-cyclopropyl-6-fluoro-1,4-dihydro-4-oxo-3-quinolinecarboxylate have been described in European Patent Application 276 700. The corresponding 7-fluoro derivatives can also be synthesized, for example, via the reaction sequence below:

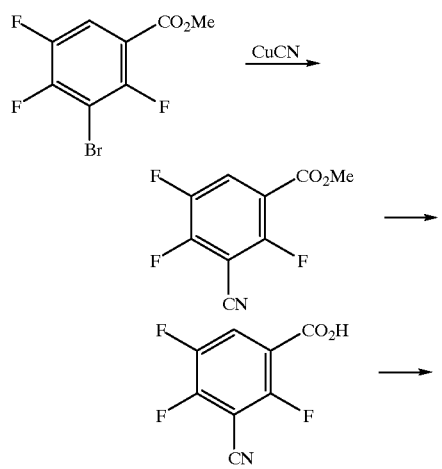

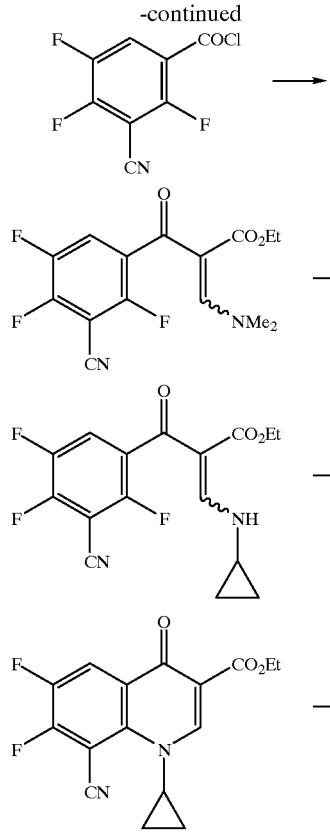

An alternative process for preparing the intermediate 2,4-dichloro-3-cyano-5-fluorobenzoyl chloride (European Patent Application 276 700), which can be converted into 3-cyano-2,4,5-trifluoro-benzoyl fluoride, starts with 5-fluoro-1,3-xylene: 5-fluoro-1,3-xylene is dichlorinated at the ring in the presence of a catalyst under ionic conditions to give 2,4-dichloro-5-fluoro-1,3-dimethylbenzene which is subsequently chlorinated in the side chains under radical conditions to give 2,4-dichloro-5-fluoro-3-dichloromethyl-1-trichloromethylbenzene. This is hydrolysed via the 2,4-dichloro-5-fluoro-3-dichloromethylbenzoic acid to give 2,4-dichloro-5-fluoro-3-formylbenzoic acid, which is subsequently converted into 2,4-dichloro-5-fluoro-3-N-hydroxyiminomethyl-benzoic acid. Treatment with thionyl chloride gives 2,4-dichloro-3-cyano-5-fluoro-benzoyl chloride which can then be converted into 3-cyano-2,4,5-trifluoro-benzoyl fluoride by chlorine-fluorine exchange.

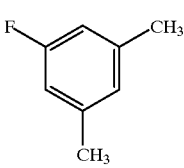

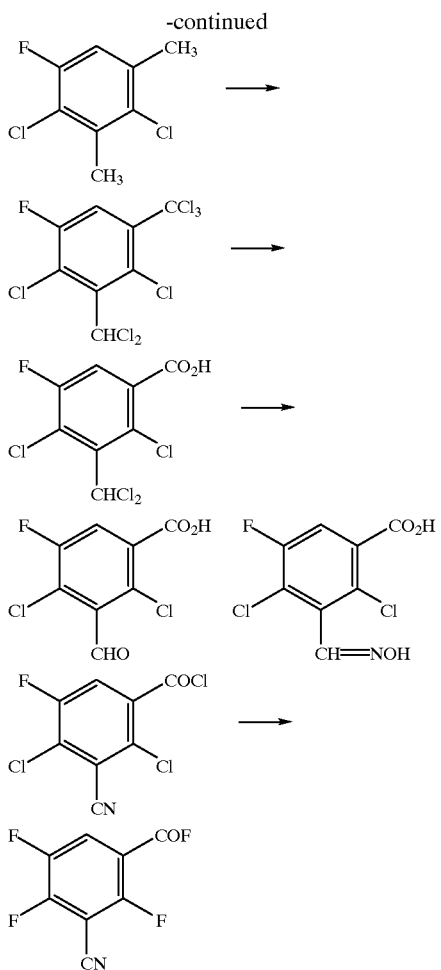

The two five-membered rings in the bicyclic bases T—H employed are cis-linked. The bases T—H can be employed as racemates or as enantiomerically pure compounds. Various processes are suitable for preparing the enantiomerically pure amines T—H:

1. The racemic bicyclic amines (T—H) can be reacted with enantiomerically pure acids, for example carboxylic acids or sulphonic acids, such as N-acetyl-L-glutamic acid, N-benzoyl-L-alanine, 3-bromo-campher-9-sulphonic acid, campher-3-carboxylic acid, cis-campheric acid, campher-10-sulphonic acid, O,O'-dibenzoyl-tartaric acid, D- or L-tartaric acid, mandelic acid, methoxyphenylacetic acid, 1-phenyl-ethanesulphonic acid, phenyl-succinic acid, to give a mixture of the diastereomeric salts which can be separated into the diastereomerically pure salts by fractional crystallization. The enantiomerically pure amines can be liberated by treating these salts with alkali metal or alkaline earth metal hydroxides.
2. In a similar manner to that described under 1., an optical resolution of the basic intermediates which are formed during the preparation of the racemic bicyclic amines can be carried out using the abovementioned enantiomerically pure acids.
3. Both the racemic amines (T—H) and some of the intermediates which lead to the bicyclic amines (T—H) can, if appropriate after acylation, be separated chromatographically on chiral supports.
4. Using chemical linkage with chiral acyl radicals, it is also possible to convert the racemic amines (T—H) into mixtures of diastereomers which can be separated by distillation, crystallization or chromatography into the diastereomerically pure acyl derivatives from which the enantiomerically pure amines can be isolated by hydrolysis. Examples of reagents for linkage with chiral acyl radicals include: methoxy-trifluoromethyl-phenylacetyl chloride, menthyl isocyanate, D- or L-phenylethyl isocyanate, menthyl chloroformate, campher-10-sulphonyl chloride.
5. During the synthesis of the bicyclic amines (T—H), it is also possible to introduce chiral instead of achiral protective groups. In this way, mixtures of diastereomers which can be separated are obtained. In the intermediate 7-benzyl-2-oxa-7-azabicyclo[3.3.0]octane-1-carbonitrile, for example, the benzyl radical can be replaced by a phenylethyl radical in the R or S configuration.

Examples of compounds according to the invention are, in addition to the compounds mentioned in the preparation examples, the compounds listed in Table 1 below, which can be employed both in racemic form and as enantiomerically pure or diastereomerically pure compounds.

TABLE 1

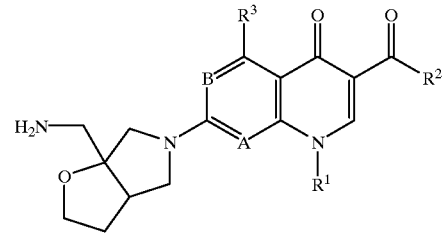

| A | B | $R^1$ | $R^2$ | $R^3$ |
|---|---|---|---|---|
| C—H | C—F | △— | OH | H |
| C—F | C—F | △— | OH | H |
| C—Cl | C—F | △— | OH | H |
| C—CH$_3$ | C—F | △— | OH | H |
| C—F | C—CN | △—F | OH | H |
| C—F | C—F | △— | OH | F |
| N | C—F | △— | OH | H |
| C—F | C—F | △— | OH | H |
| C—F | C—F | △— | OC$_2$H$_5$ | H |

TABLE 1-continued

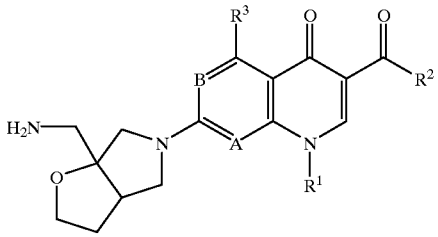

| A | B | R¹ | R² | R³ |
|---|---|---|---|---|
| C—CH₃ | C—F |  | OH | H |
| C—CH₃ | C—F |  | OH | NH₂ |
| C—F | C—F |  | OH | NH₂ |
| N | C—F |  | OH | CH₃ |
| C—H | C—F | 2,4-F₂C₆H₃ | OH | H |

The compounds according to the invention have strong antibiotic activity and display a broad antibacterial spectrum against gram-positive and gram-negative pathogens, but in particular also against Helicobacter spp., while having low toxicity.

These useful properties make it possible to use them as chemotherapeutic active compounds for the therapy of *Helicobacter pylori* infections and associated gastroduodenal disorders which can be prevented, improved and/or cured by the compounds according to the invention.

The compounds according to the invention can be administered in various pharmaceutical preparations. Preferred pharmaceutical preparations are tablets, coated tablets, capsules, pills, granules, solutions, suspensions and emulsions.

Although the compounds according to the invention are administered as monotherapeutic agents, they can also be used, if required, in combination with other therapeutics. Possible combination partners include: nitroimidazole derivatives, for example metronidazole; proton pump inhibitors, for example omeprazole, pantoprazole or lanzoprazole; $H_2$-receptor antagonists, such as, for example, cimetidine, ranitidine, famotidine or nizatidine; bismuth compounds, such as, for example, bismuth salicylate or CBS (colloidal bismuth subcitrate); other antibiotics, such as, for example, amoxicillin, azlocillin or clarithromycin; antacids.

The minimum inhibitory concentrations of some compounds according to the invention are shown in an exemplary manner as a measure for the antibacterial activity in Table 2 below, in comparison to the structurally similar 7-(1-aminomethyl-2-oxa-7-aza-bicyclo[3.3.0]oct-7-yl)-1-cyclopropyl-6,8-difluoro-1,4-dihydro-4-oxo-5-vinyl-3-quinolinecarboxylic acid (European Patent Application 671 391) and ciprofloxacin.

The minimum inhibitory concentrations (MIC) were determined in the agar dilution test on Columbia agar or basis 2 agar (Oxoid) using 10% lysed horse blood, either at pH 7 or pH 5, with 1 g of urea/l. The test substances were tested in replica dishes which contained concentrations of the active compound which decreased in each case by a dilution factor of two. For inoculation, fresh Helicobacter cultures from liquid culture or suspension of the pathogens from agar plates were used. The inoculated agar plates were incubated at 37° C. in an atmosphere containing 5–10% of $CO_2$ for 48–72 hours. The MIC value (μg/ml) which was read off is the lowest concentration of active compound at which no growth was noticeable with the naked eye. The following Helicobacter isolates were used: *H. felis* ATCC 49179, *H. pylori* NCTC 11637, *H. pylori* clinic isolate 008.

TABLE 2

MIC values (mg/l) of some compounds according to the invention in comparison to a reference compound (Ref.*) (agar dilution test)

| | MIC (mg/l) | |
|---|---|---|
| Example | H. pylori 008 | H. pylori 11637 |
| 1 B | 0.06 | 0.25 |
| 1 BA | 0.06 | 0.06 |
| 2 B | 0.06 | 0.5 |
| 5 B | 0.03 | 0.03 |
| 5 C | 0.03 | 0.03 |
| 5 D | 1 | 1 |
| 6 C | 0.03 | 0.03 |
| 9 B | <2 | <2 |
| 10 B | 0.06 | 0.06 |
| 11 B | ≦0.015 | 0.03 |
| 12 B | ≦0.015 | 0.03 |
| 12 C | ≦0.015 | 0.03 |
| 13 B | ≦0.015 | 0.03 |
| 14 B | ≦0.015 | 0.125 |
| 14 C | ≦0.015 | 0.03 |
| 16 B | 0.25 | 0.125 |
| 17 B | 0.125 | 0.25 |
| 18 B | 0.125 | 0.125 |
| 23 B | ≦0.015 | ≦0.015 |
| 24 B | 0.06 | 0.125 |
| 26 B | 0.06 | 0.25 |
| 27 | ≦0.015 | 0.5 |
| 29 | 8 | 8 |
| 30 | 0.25 | 0.125 |
| 31 | <0.5 | 0.5 |
| 34 B | 0.125 | 0.25 |
| Ciprofloxacin | 0.125 | 0.125 |
| Ref.*⁾ | 0.25 | 0.25 |

*⁾Ref. = 7-(1-aminomethyl-2-oxa-7-aza-bicyclo[3.3.0]oct-7-yl)-1-cyclopropyl-6,8-difluoro-1,4-dihydro-4-oxo-5-vinyl-3-quinolinecarboxylic acid hydrochloride (European Patent Application 671 391)

As an example of the surprisingly high in vivo activity of the compounds according to the invention, Table 3 shows the therapeutic success after a 3-day treatment of infected mice with rac. 7-(1-aminomethyl-2-oxa-7-aza-bicyclo [3.3.0]oct-7-yl)-1-cyclopropyl-6,8-difluoro-1,4-dihydro-4-oxo-3-quinolinecarboxylic acid hydrochloride and for 1S,5R-(+)-7-(1-aminomethyl-2-oxa-7-aza-bicyclo[3.3.0] oct-7-yl)-8-cyano-1-cyclopropyl-6-fluoro-1,4-dihydro-4-oxo-3-quinolinecarboxylic acid hydrochloride (Example 5 C) in comparison to the treatment with Ciprofloxacin: whereas the clearance rate with Ciprofloxacin is only 17%, it is 67% and 100%, respectively, for the compounds according to the invention. A 14-day treatment of the mice with 3×10 mg of rac. 7-(1-aminomethyl-2-oxa-7-aza-bicyclo [3.3.0]oct-7-yl)-1-cyclopropyl-6,8-difluoro-1,4-dihydro-4-oxo-3-quinolinecarboxylic acid hydrochloride/kg even resulted in a total eradication of the pathogen.

For studies in the animal model, female Swiss mice (8 to 12 weeks old, SPF breed) were kept with commercial feed and water. For colonization, a defined *H. felis* strain (ATCC 49179) was used. The bacteria were administered as a suspension (0.1 ml with 10⁸–10⁹ bacteria) 4 times within 7 days using a pharyngeal tube. Alternatively, stomach homogenates of mice which had been infected earlier were also used for infection.

3–5 days after the infection had established itself, the treatment with the test preparations was started. As a first treatment success, the reduction of the germs was determined as "clearance" 24 hours after the last treatment (for example 3, 7, 10, 14 days; 1–3 times daily). In some cases, pathogen eradication 2–4 weeks after the end of the treatment was also determined. In accordance with the "CLO" test used in clinical diagnostics, a microtitre-based urease test was used. Defined stomach biopsy specimens were tested for change of colour within a period of 24 hours.

TABLE 3

Therapeutic success after a 3-day treatment of infected mice (6 animals per group)

| Preparation | Dose [mg/kg] | Clearance | % |
| --- | --- | --- | --- |
| Substance A | 2 × 10 | 4/6 | 67 |
| Substance B | 2 × 10 | 6/6 | 100 |
| Ciprofloxacin | 2 × 10 | 1/6 | 17 |

EXAMPLES

Preparation of the Intermediates

Example I1

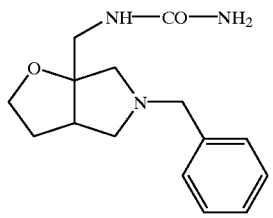

At 25° C., 4.64 g (20 mmol) of 1-aminomethyl-7-benzyl-2-oxa-7-aza-bicyclo[3.3.0]octane are dissolved in 20 ml of water with 20 ml of 1N HCl. A solution of 1.98 g (22 mmol) of potassium cyanate in 20 ml of water is added and the mixture is heated under reflux for 1 hour. The mixture is concentrated at 60° C./15 mbar, the residue is eluted with dichloromethane and the eluate is dried with sodium sulphate and concentrated. This gives an oil (7.3 g) which is purified chromatographically over silica gel using dichloromethane/methanol/17% ammonia (150:20:1).

Yield: 4.0 g (72% of theory) of 7-benzyl-1-ureidomethyl-2-oxa-7-aza-bicyclo[3.3.0]octane as an oil, ¹H-NMR (400 MHz; CDCl₃): 4.9 broad (NH₂), 5.7 ppm broad (NH).

Example I2

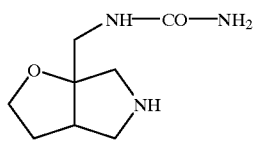

In the presence of 2 g of Pd—C, 3.9 g (14 mmol) of 7-benzyl-1-ureidomethyl-2-oxa-7-aza-bicyclo[3.3.0]octane in 70 ml of ethanol are hydrogenated at 100° C./100 bar, the catalyst is filtered off, the solution is concentrated and the resulting product (2.8 g of a viscous oil) is purified by chromatography.

Yield: 1.5 g (58% of theory) of 1-ureidomethyl-2-oxa-7-aza-bicyclo[3.3.0]octane as a viscous oil, FAB-MS: m/e 186 [(M+H)⁺], 371 [(2M+H)⁺].

Example I3

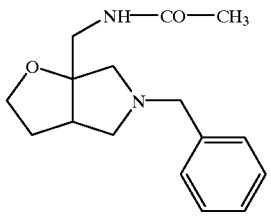

7 g (30 mmol) of 1-aminomethyl-7-benzyl-2-oxa-7-aza-bicyclo[3.3.0]octane are initially charged in 50 ml of dioxane and admixed with 3 g (30 mmol) of triethylamine, and 3 g (30 mmol) of acetic anhydride are added dropwise with ice-cooling over a period of 10 minutes. The mixture is stirred at room temperature overnight and concentrated at 60° C./20 mbar. The resulting residue is purified chromatographically over silica gel using dichloromethane/methanol/17% ammonia (150/20/1) as mobile phase.

Yield: 8.2 g of 1-acetylaminomethyl-7-benzyl-2-oxa-7-aza-bicyclo[3.3.0]octane as an oil, content (according to GC): 94%.

Mass spectrum: 274 (M⁺), 202, 184, 170, 91 (100%).

Example I4

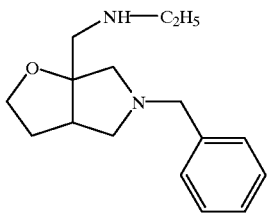

7.1 g (25.9 mmol) of 1-acetylaminomethyl-7-benzyl-2-oxa-7-aza-bicyclo[3.3.0]octane are dissolved in 50 ml of tetrahydrofuran, and this solution is added dropwise to a suspension of 3.1 g (82 mmol) of lithium aluminium hydride in 60 ml of tetrahydrofuran in such a way that the temperature is kept at from 31° to 33° C. The mixture is subsequently heated under reflux for 12 hours and decomposed with cooling with 1.2 ml of water and 1.2 ml of 15% strength aqueous sodium hydroxide solution. The precipitate is filtered off with suction and washed with tetrahydrofuran, and the filtrate is concentrated. The oil that remains (5.5 g) is purified chromatographically over silica gel (mobile phase: dichloromethane/methanol/17% strength ammonia 150:20:1).

Yield: 4.55 g (67.5% of theory) of 7-benzyl-1-ethylaminomethyl-2-oxa-7-aza-bicyclo[3.3.0]octane as an oil.

Example I5

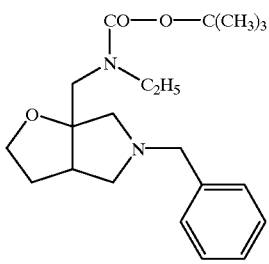

1.4 g (5.4 mmol) of 7-benzyl-1-ethylaminomethyl-2-oxa-7-aza-bicyclo[3.3.0]octane are dissolved in 6 ml of tert-butanol and admixed with a solution of 220 mg (5.5 mmol) of NaOH in 4 ml of water and 1.24 g (5.7 mmol) of di-tert-butyl dicarbonate. The temperature increases to 27°–31° C. The mixture is stirred overnight and concentrated and the residue is taken up in approximately 20 ml of water and extracted with dichloromethane. The extract is dried using sodium sulphate and concentrated under reduced pressure.

Yield: 1.58 g (81.5% of theory) of 7-benzyl-1-(N-tert-butoxycarbonyl-N-ethylaminomethyl-2-oxa-7-aza-bicyclo [3.3.0]octane as an oil.

Example I6

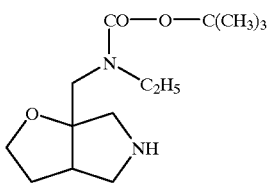

In the presence of 0.8 g of Pd—C (10%), 3.5 g (9.7 mmol) of 7-benzyl-1-(N-tert-butoxycarbonyl-N-ethylaminomethyl)-2-oxa-7-aza-bicyclo[3.3.0]octane in 60 ml of ethanol are hydrogenated at 70° C./90 bar. The catalyst is filtered off and washed with ethanol and the filtrate is concentrated. The residue is purified chromatographically over silica gel (mobile phase: dichloromethane/methanol 95:5).

Yield: 2.0 g (76% of theory) of 1-(N-tert-butoxycarbonyl-N-ethylaminomethyl)-2-oxa-7-aza-bicyclo[3.3.0]octane as an oil.

Example I7

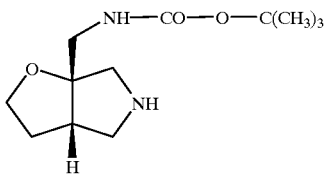

A: 7-Benzyl-1-cyano-2-oxa-7-azabicyclo[3.3.0]octane(5-benzyl-hexahydrofuro[2,3-c]pyrrole-6a-carbonitrile) is prepared according to the procedure of European Patent Application 589 318 and purified chromatographically (silica gel, dichloromethane). This racemic compound is separated into the enantiomers via a chromatographic optical resolution (support: Daicel-Chiracell OJ), and the enantiomers are reacted further via the subsequent steps, in accordance with the procedures of European Patent Application 589 318.

B: 1.67 g (7.3 mmol) of (−)-7-benzyl-1-cyano-2-oxa-7-azabicyclo[3.3.0]octane in 23 ml of absolute tetrahydrofuran are reduced under reflux with 362 mg of lithium aluminium hydride for 15 hours. The suspension is admixed with aqueous potassium hydroxide solution, inorganic salts are filtered off with suction and the filtrate is concentrated and purified by chromatography (silica gel, dichloromethane/methanol 2:1).

Yield: 1.30 g (76.6% of theory) of (−)-1-aminomethyl-7-benzyl-2-oxa-7-azabicyclo[3.3.0]octane as an oil, $[\alpha]^0$: −6.9° (c=1.3, dichloromethane).

C: 1.2 g (5.2 mmol) of (−)-1-aminomethyl-7-benzyl-2-oxa-7-azabicyclo[3.3.0]octane in 6.5 ml of tert-butanol are admixed with 254 mg of NaOH in 5.1 ml of water, 1.3 g of di-tert-butyl pyrocarbonate are added and the mixture is stirred at room temperature for approximately 30 minutes. The mixture is extracted with dichloromethane and the extract is dried with potassium carbonate and concentrated. The resulting crude product is purified chromatographically (silica gel/dichloromethane 10:1).

Yield: 1.69 g (98% of theory) of (−)-(1S,5S)-1-tert-butoxycarbonylaminomethyl-7-benzyl-2-oxa-7-aza-bicyclo [3.3.0]octane as an oil, $[\alpha]^0$: −11.8° (c=1.16, dichloromethane).

D: 1.56 g (4.49 mmol) of (−)-(1S,5S)-1-tert-butoxycarbonylaminomethyl-7-benzyl-2-oxa-7-aza-bicyclo [3.3.0]octane in 50 ml of ethanol are hydrogenated at 100° C./90 bar in the presence of 0.5 g of Pd—C (10%). The mixture is filtered, the filtrate is concentrated and the residue is chromatographed over silica gel using dichloromethane/methanol/17% ammonia (150:20:1) as mobile phase. The concentrated eluate crystallizes through.

Yield: 790 mg (73% of theory) of (−)-(1S,5S)-1-tert-butoxycarbonylaminomethyl-2-oxa-7-aza-bicyclo[3.3.0] octane, Melting point: 104–105° C., $[\alpha]^6$: −10.2° (0.56, CHCl$_3$).

Example I8

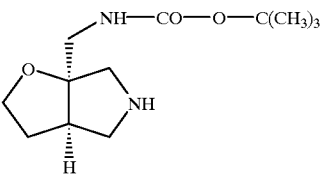

5.6 g (16.8 mmol) of (+)-(1R,5R)-1-tert-butoxycarbonylaminomethyl-7-benzyl-2-oxa-7-aza-bicyclo [3.3.0]octane, $[\alpha]^0$: +13.1° (c=1.1, dichloromethane), which is prepared analogously to the procedures in Examples I7 A to C, are hydrogenated in 100 ml of ethanol at 70° C./20 bar in the presence of 1 g of Pd—C (10%). The mixture is filtered, the filtrate is concentrated and the residue (3.5 g) is chromatographed over silica gel using dichloromethane/methanol (95:5) as mobile phase. The concentrated eluate crystallizes through.

Yield: 2.54 g (63% of theory) of (+)-(1R,5R)-1-tert-butoxycarbonylaminomethyl-2-oxa-7-azabicyclo[3.3.0] octane, Melting point: 102–103° C.,
$[\alpha]^6$: +7.0° (0.3, CHCl$_3$).

Example I9A

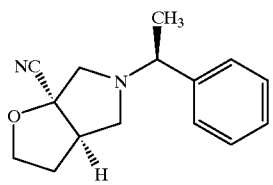

A solution of 83 g (0.87 mol) of 2-cyano-4,5-dihydrofuran in 2000 ml of absolute ethyl acetate is initially charged at 15° C. At this temperature, first 0.5 ml of trifluoroacetic acid and then 227 g (0.77 mol, 85% strength) of N-methoxymethyl-N-[(S)-1-phenylethyl]-N-trimethylsilylmethylamine are added dropwise over a period of 10 minutes to this solution. During the addition, the temperature increases to 45° C. The reaction mixture is stirred at room temperature overnight and subsequently washed with 200 ml of saturated sodium bicarbonate solution. The organic phase is dried over sodium sulphate and concentrated under reduced pressure. The crude product is purified by silica gel column chromatography (toluene/ethyl acetate, 99:1), giving a mixture of diastereomers (56 g, ratio of the diastereomers A:B=1.6:1). For crystallization, the residue is dissolved in 100 ml of diethyl ether and slowly cooled to –35° C. The crystals which have precipitated out are filtered off through a cooled frit and washed with a little diethyl ether which had been cooled to 60° C.

Yield: 13.3 g (7.1% of theory) of (1R,5R)-1-cyano-7-[(S)-1-phenylethyl]-2-oxa-7-azabicyclo[3.3.0]octane (diastereomer A), Melting point: 68° C., $[\alpha]^5$: –34° (c=0.99, methanol). The absolute configuration was determined by X-ray structure analysis.

Example I9B

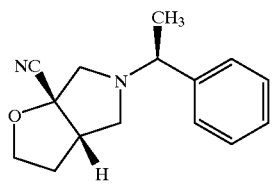

The diastereomer B is obtained as the maleic acid salt by selective crystallization from the mixture which earlier gave the diastereomer A. To a solution of the mother liquor from Example I9A (103.3 g, 0.427 mol; ratio of diastereomers: 31:69, A:B) in 2l of ethyl acetate, for example, are added 49.5 g (0.427 mol) of maleic acid. The mixture is heated under reflux for 2 hours and cooled to room temperature overnight.

The crystals are subsequently filtered off with suction and shaken in ethyl acetate and 1N aqueous sodium hydroxide solution and the organic phase is dried and concentrated. This gives the diastereomer B in a purity of >96% ee.

Yield: 32 g (45% of theory) of (1S,5S)-1-cyano-7-[(S)-1-phenylethyl]-2-oxa-7-azabicyclo[3.3.0]octane (diastereomer B).

The ethyl acetate solution which is enriched with the maleic acid salt of the diastereomer A is repeatedly extracted with water, and the aqueous phase is adjusted to pH 8 and extracted with ethyl acetate. The organic phase is subsequently dried and concentrated, giving a mixture of isomers which is enriched with diastereomer A. This isomer mixture can now be used to carry out the selective crystallization of the diastereomer A from ethyl acetate as described in Example I9A.

In this manner, the mixture of diastereomers can be separated completely in several steps, so that the yield from Example I9A can be increased to approximately 16% of theory or 26%, based on the proportion of diastereomer A.

Example 10A

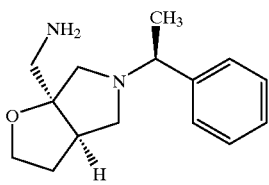

At 30° C., a solution of 16.1 g (0.067 mol) of (1R,5R)-1-cyano-7-[(S)-1-phenylethyl]-2-oxa-7-azabicyclo[3.3.0]octane in 70 ml of absolute tetrahydrofuran is added dropwise to 3.15 g (0.083 mol) of lithium aluminium hydride in 70 ml of absolute tetrahydrofuran. The reaction mixture is then heated under reflux for 15 hours and subsequently cooled to 10° C. and admixed successively with 3.5 ml of water, 3.5 ml of 15% strength potassium hydroxide solution and 3.5 ml of water. The precipitate is filtered off and washed with tetrahydrofuran and the filtrate is subsequently concentrated under reduced pressure.

Yield: 15.9 g of (1S,5R)-1-aminomethyl-7-[(S)-1-phenylethyl]-2-oxa-7-azabicyclo[3.3.0]octane as crude product, $[\alpha]^5$: –38.0° (c=1.21, methanol).

Example I10B

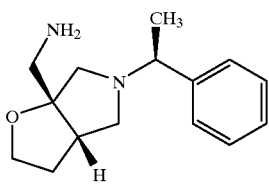

50 ml of liquid ammonia and 5 g of Raney nickel are added to a solution of 15 g (0.062 mol) of (1R,5S)-1-cyano-7-[(S)-1-phenylethyl]-2-oxa-7-azabicyclo-[3.3.0]octane in 30 ml of tetrahydrofuran, and the mixture is then hydrogenated at 80° C. under a hydrogen pressure of from 110 to 120 bar for 5 hours. After the reaction has gone to completion, the mixture is filtered through Celite and concentrated.

Yield: 12.5 g (82% of theory) of (1R,5S)-1-aminomethyl-7-[(S)-1-phenylethyl]-2-oxa-7-azabicyclo[3.3.0]octane.

Example I11

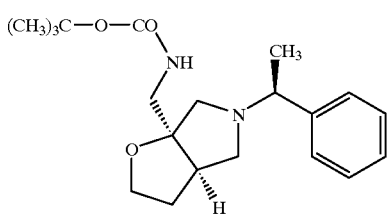

At 10° C., 6.4 g (0.6 mol) of sodium carbonate and 13.0 g (0.6 mol) of di-tert-butyl dicarbonate are added successively to a solution of 13.4 g (0.545 mol) of (1S,5R)-1-aminomethyl-7-[(S)-1-phenylethyl]-2-oxa-7-azabicyclo[3.3.0]octane in 60 ml of dioxane. The mixture is stirred at room temperature for one hour and subsequently concentrated under reduced pressure. The residue is purified by silica gel column chromatography (dichloromethane/methanol, 95:5).

Yield: 18.9 g (quantitative) of (1S,5R)-1-tert-butoxycarbonylaminomethyl-7-[(S)-1-phenylethyl]-2-oxa-7-azabicyclo[3.3.0]octane, $[\alpha]^5$: −19.0° (c=1.5 in methanol).

Example I12

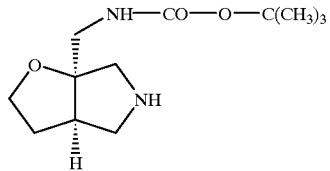

18.0 g (0.052 mol) of (1S,5R)-1-tert-butoxycarbonylaminomethyl-7-[(S)-1-phenylethyl]-2-oxa-7-azabicyclo[3.3.0]octane are dissolved in 150 ml of absolute methanol and, after addition of 2.5 g of 10% palladium-activated carbon, hydrogenated at 70° C. and 20 bar for 9 h. The catalyst is filtered off and the filtrate is concentrated under reduced pressure.

Yield: 12.5 g (99% of theory) of (1R,5R)-1-tert-butoxycarbonylaminomethyl-2-oxa-7-azabicyclo[3.3.0]octane, $[\alpha]^6$: +11.9° (c=0.7, methanol).

Treatment of (1R,5R)-1-tert-butoxycarbonylaminomethyl-2-oxa-7-azabicyclo-[3.3.0]octane with concentrated hydrochloric acid at room temperature gives (1S,5R)-1-aminomethyl-2-oxa-7-azabicyclo[3.3.0]octane hydrochloride.

Example I13

Ethyl 8-cyano-1-cyclopropyl-6,7-difluoro-1,4-dihydro-4-oxo-3-quinoline-carboxylate

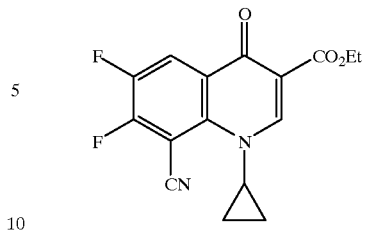

A. Methyl 3-bromo-2,4,5-trifluoro-benzoate: with ice-cooling, 772 g of 3-bromo-2,4,5-trifluoro-benzoyl fluoride are added dropwise to a mixture of 1460 ml of methanol and 340 g of triethylamine. The mixture is stirred at room temperature for 1 hour. The reaction mixture is concentrated, the residue is taken up in water and methylene chloride and the aqueous phase is extracted with methylene chloride. The organic phase is dried over sodium sulphate and then concentrated, and the residue is distilled under reduced pressure. This gives 752.4 g of methyl 3-bromo-2,4,5-trifluoro-benzoate of boiling point 122° C./20 mbar.

B. Methyl 3-cyano-2,4,5-trifluoro-benzoate: 269 g of methyl 3-bromo-2,4,5-trifluoro-benzoate and 108 g of copper cyanide in 400 ml of dimethylformamide are heated at reflux for 5 hours. All volatile components of the reaction mixture are subsequently distilled off under reduced pressure. The distillate is then fractionated over a column. This gives 133 g of methyl 3-cyano-2,4,5-trifluoro-benzoate of boiling point 88–89° C./0.01 mbar.

C. 3-Cyano-2,4,5-trifluoro-benzoic acid: a solution of 156 g of methyl 3-cyano-2,4,5-trifluoro-benzoate in 960 ml of glacial acetic acid, 140 ml of water and 69 ml of concentrated sulphuric acid is heated at reflux for 8 hours. Most of the acetic acid is subsequently distilled off under reduced pressure and the residue is admixed with water. The precipitated solid is filtered off with suction, washed with water and dried. This gives 118.6 g of 3-cyano-2,4,5-trifluoro-benzoic acid as a white solid of melting point 187–190° C.

D. 3-Cyano-2,4,5-trifluoro-benzoyl chloride: 111 g of 3-cyano-2,4,5-trifluorobenzoic acid and 84 g of oxalyl chloride in 930 ml of dry methylene chloride are, with addition of a few drops of dimethylformamide, stirred at room temperature for 5 hours. The methylene chloride is subsequently stripped off and the residue is distilled under reduced pressure. This gives 117.6 g of 3-cyano-2,4,5-trifluoro-benzoyl chloride as a yellow oil.

E. Ethyl 2-(3-cyano-2,4,5-trifluoro-benzoyl)-3-dimethylamino-acrylate: a solution of 55 g of 3-cyano-2,4,5-trifluoro-benzoyl chloride in 50 ml of toluene is added dropwise to a solution of 36.5 g of ethyl 3-dimethylamino-acrylate and 26.5 g of triethylamine in 140 ml of toluene in such a way that the temperature remains between 50 and 55° C. The mixture is then stirred at 50° C. for another 2 hours. The reaction mixture is concentrated under reduced pressure and used for the next step without further work-up.

F. Ethyl 2-(3-cyano-2,4,5-trifluoro-benzoyl)-3-cyclopropylamino-acrylate: at 20° C., 30 g of glacial acetic acid are added dropwise to the reaction product from step E. A solution of 15.75 g of cyclopropylamine in 30 ml of toluene is subsequently added dropwise. The mixture is stirred at 30° C. for 1 hour. 200 ml of water are then added, the mixture is stirred for 15 minutes and the organic phase is separated off and once more shaken with 100 ml of water. The organic phase is then dried over sodium sulphate and concentrated under reduced pressure. The resulting crude product is used for the next step without further work-up.

G. Ethyl 8-cyano-1-cyclopropyl-6,7-difluoro-1,4-dihydro-4-oxo-3-quinolinecarboxylate: the reaction product from step F and 27.6 g of potassium carbonate in 80 ml of dimethylformamide are stirred at room temperature for 16 hours. The reaction mixture is then added to 750 ml of ice-water and the solid is filtered off with suction and washed with 80 ml of cold methanol. Drying gives 47 g of ethyl 8-cyano-1-cyclopropyl-6,7-difluoro-1,4-dihydro-4-oxo-3-quinolinecarboxylate of melting point 209–211° C.

Example I14

2,4-Dichloro-5-fluoro-1,3-dimethylbenzene

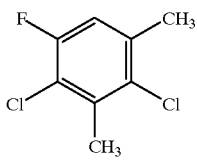

a) Solvent-free 1 g of anhydrous iron(III) chloride is initially charged in 124 g of 3,5-dimethylfluorobenzene and chlorine is introduced (approximately 4 h) at the rate of its consumption. The reaction is initially slightly exothermic (temperature increase from 24 to 32° C.) and the temperature is kept below 30° C. by cooling. After the introduction of 120 g of chlorine, the mixture solidifies. According to GC analysis, 33.4% of monochloro compound, 58.4% of the desired product and 5% of more highly chorinated compounds have been formed. The hydrogen chloride is removed and the reaction mixture is subsequently distilled over a column under water pump vacuum:

The initial fraction gives, at 72–74° C./22 mbar, 49 g of 2-chloro-5-fluoro-1,3-dimethylbenzene. After an intermediate fraction of 5 g, 75 g of 2,4-dichloro-5-fluoro-1,3-dimethylbenzene are distilled over at 105° C./22 mbar; melting range: 64–65° C.

b) In 1,2-dichloroethane 1 kg of 3,5-dimethyl-fluorobenzene and 15 g of anhydrous iron(III) chloride are initially charged in 1 l of 1,2-dichloroetane and chlorine is introduced at the rate of its consumption (approximately 4 h). Initially, the reaction is exothermic (temperature increase from 24 to 32° C.), and the temperature is kept below 30° C. by cooling. After the introduction of 1200 g of chlorine, GC analysis shows that 4% of the monochloro compound, 81.1% of the desired product and 13.3% of more highly chlorinated compounds have been formed. Solvent and hydrogen chloride are distilled off and the residue is then distilled over a column under water pump vacuum:

The initial fraction gives 40 g of 2-chloro-5-fluoro-1,3-dimethylbenzene. After a small intermediate fraction, 1115 g of 2,4-dichloro-5-fluoro-1,3-dimethylbenzene are distilled over at 127–128° C./50 mbar.

Example I15

2,4-Dichloro-5-fluoro-3-dichloromethyl-1-trichloromethylbenzene

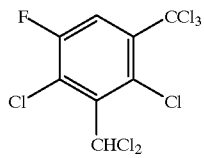

In a photochlorination apparatus fitted with a chlorine inlet and an outlet for the hydrogen chloride to a washer and a light source in the vicinity of the chlorine inlet tube, 1890 g of 2,4-dichloro-5-fluoro-1,3-dimethylbenzene are initially charged, and chlorine is metered in at from 140 to 150° C. Over a period of 30 h, 3850 g of chlorine are introduced. According to GC analysis, the content of desired product is 71.1%; the proportion of underchlorinated compounds is 27.7%.

Distillation over a 60 cm column with Wilson spirals gives an initial fraction of 1142 g which can be recycled into the chlorination. The main fraction at 160–168° C./0.2 mbar gives 2200 g of 2,4-dichloro-5-fluoro-3-dichloromethyl-1-trichloromethylbenzene of a melting range of 74–76° C. After recrystallization of a sample from methanol, the melting point is 81–82° C.

Example I16

2,4-Dichloro-5-fluoro-3-formyl-benzoic Acid

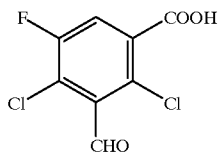

In a stirred apparatus with gas outlet, 2500 ml of 95% strength sulphuric acid are initially charged at 70° C., and 500 g of molten 2,4-dichloro-5-fluoro-3-dichloromethyl-1-trichloromethylbenzene are added dropwise with stirring. Evolution of hydrogen chloride starts after a short while. Metered addition is continued for 2 h and the mixture is stirred until the evolution of gas ceases. After cooling to 20° C., the mixture is discharged under 4 kg of ice and the precipitated solid is filtered off with suction. The product is washed with water and dried.

Yield: 310 g,
Melting range: 172–174° C.

Example I17

2,4-Dichloro-5-fluoro-3-N-hydroxyiminomethyl-benzoic Acid

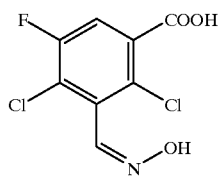

In a stirred apparatus, 80 g of hydroxylammonium chloride are initially charged in 500 ml of ethanol, 200 ml of 45% strength aqueous sodium hydroxide solution are added dropwise and, at 40–45° C., 200 g of 2,4-dichloro-5-fluoro-3-formyl-benzoic acid are subsequently introduced. The reaction is slightly exothermic, and stirring is continued at 60° C. for 5 h. After cooling to room temperature, the pH is adjusted to <3 by dropwise addition of hydrochloric acid, the product is taken up in tert-butyl methyl ether, the organic phase is separated off and the solvent is distilled off. 185 g of 2,4-dichloro-5-fluoro-3-N-hydroxyiminomethyl-benzoic acid are obtained as residue; melting range: 190–194° C.

Example I18
2,4-Dichloro-3-cyano-5-fluoro-benzoyl Chloride

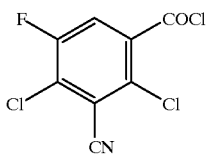

In a stirred apparatus fitted with a metering device and a gas outlet via a reflux condenser to a washer, 600 ml of thionyl chloride are initially charged and, at 20° C., 210 g of 2,4-dichloro-5-fluoro-3-N-hydroxyiminomethyl-benzoic acid are introduced at the rate at which hydrogen chloride and sulphur dioxide are formed. After the addition, the mixture is heated under reflux until evolution of gas has ceased. The mixture is subsequently distilled, giving, in a boiling range of 142–145° C./10 mbar, 149 g of 2,4-dichloro-3-cyano-5-fluoro-benzoyl chloride (content according to GC: 98.1%); melting range: 73–75° C.

Example I19
3-Cyano-2,4,5-trifluoro-benzoyl Fluoride

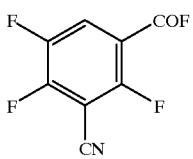

50 g of potassium fluoride are suspended in 120 ml of tetramethylene sulphone and, at 15 mbar, subjected to incipient distillation (approximately 20 ml) for drying. 50.4 g of 2,4-dichloro-3-cyano-5-fluoro-benzoyl chloride are subsequently added and the mixture is stirred with exclusion of moisture at an internal temperature of 180° C. for 12 hours. Vacuum distillation gives 32.9 g of 3-cyano-2,4,5-trifluoro-benzoyl fluoride with a boiling range of 98–100° C./12 mbar.

Example I20
3-Cyano-2,4,5-trifluoro-benzoyl Chloride

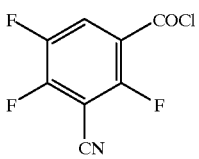

76.6 g of 3-cyano-2,4,5-trifluoro-benzoyl fluoride, together with 1 g of anhydrous aluminium chloride, are initially charged at 60–65° C., and 25 g of silicon tetrachloride are then added dropwise at the rate at which gas is given off. After the evolution of gas has ceased at 65° C., the mixture is distilled under reduced pressure. In the boiling range of 120–122° C./14 mbar, 73.2 g of 3-cyano-2,4,5-trifluoro-benzoyl chloride distil over.

Example I21

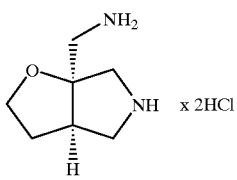

0.5 g (2.07 mmol) of (1R,5R)-1-tert-butoxycarbonylaminomethyl-2-oxa-7-azabicyclo[3.3.0]octane in 30 ml of ethanol are admixed with 13 ml of approximately 3.5 N hydrochloric acid, and the mixture is stirred at room temperature for 4 hours. The mixture is concentrated and the salt is isolated.

Yield: 0.3 g (67.5% of theory) of (1S,5R)-1-aminomethyl-2-oxa-7-azabicyclo[3.3.0]octane dihydrochloride, Melting point: 284° C., $[\alpha]^4$: +16.5° (c=1, methanol).

(1R,5S)-1-Aminomethyl-2-oxa-7-azabicyclo[3.3.0]octane dihydrochloride and (1SR,5RS)-1-aminomethyl-2-oxa-7-azabicyclo[3.3.0]octane dihydrochloride are also obtained correspondingly.

Preparation of the Active Compounds

Example 1

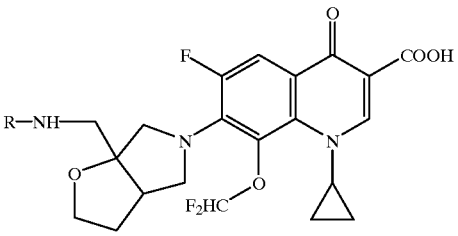

A. R = (CH$_3$)$_3$C——O——CO
B. R = H x HCl

A: A mixture of 332 mg (1 mmol) of 1-cyclopropyl-8-difluoromethoxy-6,7-difluoro-1,4-dihydro-4-oxo-3-quinolinecarboxylic acid in 4 ml of acetonitrile and 2 ml of dimethylformamide with 112 mg (1 mmol) of 1,4-diazabicyclo[2.2.2]octane and 267 mg (1.1 mmol) of 1-tert-butoxycarbonylaminomethyl-2-oxa-7-aza-bicyclo[3.3.0]octane is heated under reflux for 1 hour. The suspension is concentrated at 70° C./15 mbar and the residue is admixed with a little water and treated in an ultrasonic bath for 30 minutes. The undissolved precipitate is filtered off with suction, washed with water and dried at 90° C. under high vacuum.

Yield: 487 mg (88% of theory) of 7-(1-tert-butoxycarbonylaminomethyl-2-oxa-7-aza-bicyclo[3.3.0]oct-7-yl)-1-cyclopropyl-8-difluoromethoxy-6-fluoro-1,4-dihydro-4-oxo-3-quinolinecarboxylic acid, Melting point: 215–217° C. (decomposition).

B. 476 mg (0.86 mmol) of 7-(1-tert-butoxycarbonylaminomethyl-2-oxa-7-aza-bicyclo[3.3.0]oct-7-yl)-1-cyclopropyl-8-difluoromethoxy-6-fluoro-1,4-dihydro-4-oxo-3-quinolinecarboxylic acid are dissolved in 5 ml of hot, half-concentrated hydrochloric acid, and the solution is filtered and concentrated at 60° C./15 mbar. The residue is admixed with a little ethanol and reconcentrated, and the salt is isolated and dried at 90° C. under high vacuum.

Yield: 385 mg (91% of theory) of 7-(1-aminomethyl-2-oxa-7-aza-bicyclo[3.3.0]oct-7-yl)-1-cyclopropyl-8-difluoromethoxy-6-fluoro-1,4-dihydro-4-oxo-3-quinolinecarboxylic acid hydrochloride, Melting point: 182–185° C. (decomposition).

AA. By the method of step A, (+)-(1R,5R)-1-tert-butoxycarbonylaminomethyl-2-oxa-7-aza-bicyclo[3.3.0]octane is converted into (+)-(1R,5R)-7-(1-tert-butoxycarbonylaminomethyl-2-oxa-7-aza-bicyclo[3.3.0]oct-7-yl)-1-cyclopropyl-8-difluoromethoxy-6-fluoro-1,4-dihydro-4-oxo-3-quinolinecarboxylic acid.

Melting point: 166–167° C. (decomposition), $[\alpha]^5$: +26° (c=0.25, DMF).

BA. By the method of step B, the product from step AA is converted into (−)-(1S,5R)-7-(1-aminomethyl-2-oxa-7-aza-bicyclo[3.3.0]oct-7-yl)-1-cyclopropyl-fluoromethoxy-6-fluoro-1,4-dihydro-4-oxo-3-quinolinecarboxylic acid hydrochloride.

Melting point: 194–197° C. (decomposition), $[\alpha]^5$: −21° (c=0.5, DMF).

AB. By the method of step A, (−)-(1S,5S)-1-tert-butoxycarbonylaminomethyl-2-oxa-7-aza-bicyclo[3.3.0]octane is converted into (−)-(1S,5S)-7-(1-tert-butoxycarbonylaminomethyl-2-oxa-7-aza-bicyclo[3.3.0]oct-7-yl)-1-cyclopropyl-8-difluoromethoxy-6-fluoro-1,4-dihydro-4-oxo-3-quinolinecarboxylic acid.

Melting point: 166–167° C. (decomposition), $[\alpha]^5$: −27° (c=0.125, DMF).

BB. By the method of step B, the product from step AB is converted into (+)-(1R,5S)-7-(1-aminomethyl-2-oxa-7-aza-bicyclo[3.3.0]oct-7-yl)-1-cyclopropyl-8-difluoromethoxy-6-fluoro-1,4-dihydro-4-oxo-3-quinolinecarboxylic acid hydrochloride.

Melting point: 194–197° C. (decomposition), $[\alpha]^5$: +19° (c=0.5, DMF).

Example 2

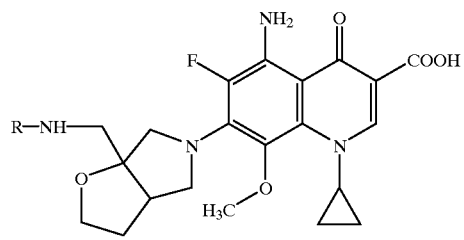

A. R = (CH₃)₃C——O——CO
B. R = H x HCl
C. R = H

A: By the method of Example 1A, 5-amino-1-cyclopropyl-6,7-difluoro-1,4-dihydro-8-methoxy-4-oxo-3-quinolinecarboxylic acid are converted into 5-amino-7-(1-tert-butoxycarbonylaminomethyl-2-oxa-7-aza-bicyclo[3.3.0]oct-7-yl)-1-cyclopropyl-6-fluoro-1,4-dihydro-8-methoxy-4-oxo-3-quinolinecarboxylic acid (77% of theory) of melting point 219–221° C. (decomposition) (after chromatographic purification over silica gel using dichloromethane/methanol/17% aqueous ammonia 150/20/1 as mobile phase).

B: By method of Example 1B, 405 mg (0.76 mmol) of the product from step A are reacted with 7 ml of half-concentrated hydrochloric acid.

Yield: 244 mg (69% of theory) of 5-amino-7-(1-aminomethyl-2-oxa-7-aza-bicyclo[3.3.0]oct-7-yl)-1-cyclopropyl-6-fluoro-1,4-dihydro-8-methoxy-4-oxo-3-quinolinecarboxylic acid hydrochloride, Melting point: 242–244° C. (decomposition).

FAB-MS: m/e 433 [(M+H)⁺].

C: 235 mg (0.44 mmol) of the product from step A are dissolved at room temperature in 20 ml of dichloromethane and admixed with 1.4 ml of trifluoroacetic acid. The mixture is stirred at room temperature for 3 hours and then concentrated, and the residue is evaporated twice with ethanol. This gives 148 mg of 5-amino-7-(1-aminomethyl-2-oxa-7-aza-bicyclo[3.3.0]oct-7-yl)-1-cyclopropyl-6-fluoro-1,4-dihydro-8-methoxy-4-oxo-3-quinolinecarboxylic acid trifluoroacetate as crude product which is purified over 40 g of silica gel using dichloromethane/methanol/17% aqueous ammonia (150/20/1) as mobile phase, giving the betain.

Yield: 69 mg (36% of theory) of 5-amino-7-(1-aminomethyl-2-oxa-7-aza-bicyclo[3.3.0]oct-7-yl)-1-cyclopropyl-6-fluoro-1,4-dihydro-8-methoxy-4-oxo-3-quinolinecarboxylic acid, Melting point: 209–211° C. (decomposition).

Example 3

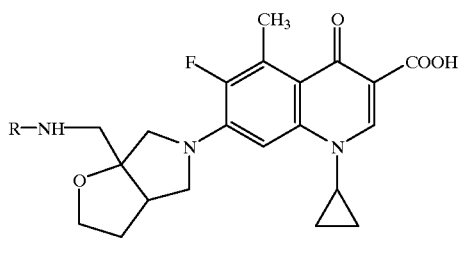

A. R = (CH₃)₃C——O——CO
B. R = H x HCl

A: By the method of Example 1A, 1-cyclopropyl-6,7-difluoro-1,4-dihydro-5-methyl-4-oxo-3-quinolinecarboxylic acid are converted into 7-(1-tert-butoxycarbonylaminomethyl-2-oxa-7-aza-bicyclo[3.3.0]oct-7-yl)-1-cyclopropyl-6-fluoro-1,4-dihydro-5-methyl-4-oxo-3-quinolinecarboxylic acid (76% of theory).

B: By the method of Example 1B, the product from step A is reacted with half-concentrated hydrochloric acid to give 7-(1-aminomethyl-2-oxa-7-aza-bicyclo[3.3.0]oct-7-yl)-1-cyclopropyl-6-fluoro-1,4-dihydro-5-methyl-4-oxo-3-quinolinecarboxylic acid hydrochloride of melting point 251–253° C. (decomposition).

Example 4

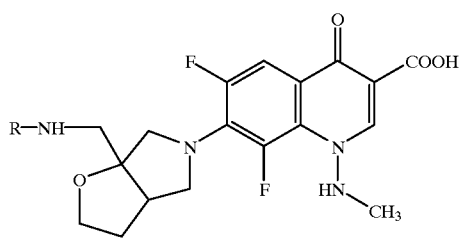

A. R = (CH₃)₃C—O—CO
B. R = H x HCl

A: By the method of Example 1A, 6,7,8-trifluoro-1,4-dihydro-1-methylamino4-oxo-3-quinolinecarboxylic acid are converted into 7-(1-tert-butoxycarbonylaminomethyl-2-oxa-7-aza-bicyclo[3.3.0]oct-7-yl)-6,8-difluoro-1,4-dihydro-1-methylamino-4-oxo-3-quinolinecarboxylic acid (68% of theory) of melting point 225–227° C. (decomposition).

B: By the method of Example 1B, the product from step A is reacted with half-concentrated hydrochloric acid to give, in a yield of 65%, 7-(1-aminomethyl-2-oxa-7-aza-bicyclo[3.3.0]oct-7-yl)-6,8-difluoro-1,4-dihydro-1-methylamino-4-oxo-3-quinolinecarboxylic acid hydrochloride of melting point 177–179° C. (decomposition). FAB-MS: m/e: 395 [(M+H)⁺], 366.

Example 5

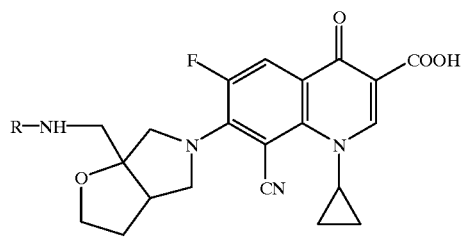

A. R = (CH₃)₃C—O—CO
B. R = H x HCl

A. R=(CH₃)₃C—O—CO
B. R=H×HCl

A: By the method of Example 1A, 7-chloro-8-cyano-1-cyclopropyl-6-fluoro-1,4-dihydro-4-oxo-3-quinolinecarboxylic acid (European Patent 276 700) is converted into 7-(1-tert-butoxycarbonylaminomethyl-2-oxa-7-aza-bicyclo[3.3.0]oct-7-yl)-8-cyano-1-cyclopropyl-6-fluoro-1,4-dihydro-4-oxo-3-quinolinecarboxylic acid.

B: By the method of Example 1B, the product from step A is reacted with half-concentrated hydrochloric acid to give 7-(1-aminomethyl-2-oxa-7-aza-bicyclo[3.3.0]oct-7-yl)-8-cyano-1-cyclopropyl-6-fluoro-1,4-dihydro-4-oxo-3-quinolinecarboxylic acid hydrochloride of melting point 241° C. (decomposition).

C. By the method of the reactions in steps A and B, (+)-1-tert-butoxycarbonylaminomethyl-2-oxa-7-aza-bicyclo[3.3.0]octane gives (+)-7-(1-aminomethyl-2-oxa-7-aza-bicyclo[3.3.0]oct-7-yl)-8-cyano-1-cyclopropyl-6-fluoro-1,4-dihydro-4-oxo-3-quinolinecarboxylic acid hydrochloride,
Melting point: 293° C. (decomposition),
$[\alpha]^4$: +50.6° (c=0.7, methanol).

D. By the method of the reactions in steps A and B, (−)-1-tert-butoxycarbonylaminomethyl-2-oxa-7-aza-bicyclo[3.3.0]octane gives (−)-7-(1-aminomethyl-2-oxa-7-aza-bicyclo[3.3.0]oct-7-yl)-8-cyano-1-cyclopropyl-6-fluoro-1,4-dihydro-4-oxo-3-quinolinecarboxylic acid hydrochloride,
Melting point: 292° C. (decomposition),
$[\alpha]^4$: −49° (c=1, methanol).

E: A solution of 5.4 g (0.224 mmol) of (1R,5R)-1-tert-butoxycarbonylaminomethyl-2-oxa-7-azabicyclo[3.3.0]octane, 6.5 g (0.204 mol) of ethyl 8-cyano-1-cyclopropyl-6,7-difluoro-1,4-dihydro-4-oxo-3-quinolinecarboxylate and 4.6 g (0.459 mol) of triethylamine and 300 ml of absolute acetonitrile is stirred at room temperature overnight. The mixture is subsequently concentrated under reduced pressure and the residue is chromatographed over silica gel (dichloromethane/methanol, 99:1→95:5). This gives 9.2 g (83.6% of theory) of ethyl (+)-7-[(1R,5R)-1-tert-butoxycarbonylaminomethyl-2-oxa-7-aza-bicyclo[3.3.0]oct-7-yl]-8-cyano-1-cyclopropyl-6-fluoro-1,4-dihydro-4-oxo-quinolinecarboxylate,
$[\alpha]^4$: +81.1° (c=1.5, dichloromethane).

9.1 g (0.169 mol) of ethyl (+)-7-[(1R,5R)-1-tert-butoxycarbonylaminomethyl-2-oxa-7-aza-bicyclo[3.3.0]oct-7-yl]-8-cyano-1-cyclopropyl-6-fluoro-1,4-dihydro-4-oxo-quinolinecarboxylate are admixed with 150 ml of 10% strength hydrochloric acid. The mixture is heated under reflux for 1 hour and subsequently cooled to room temperature. The colourless crystals are filtered off and washed with a little absolute isopropanol.

Yield: 6.9 g (91% of theory) of (+)-7-[(1S,5R)-1-aminomethyl-2-oxa-7-azabicyclo[3.3.0]oct-7-yl]-8-cyano-1-cyclopropyl-6-fluoro-1,4-dihydro-4-oxo-quinolinecarboxylic acid hydrochloride,
Melting point: 293° C.,
$[\alpha]^4$: +50.60° (c=0.8 in methanol).

Example 6

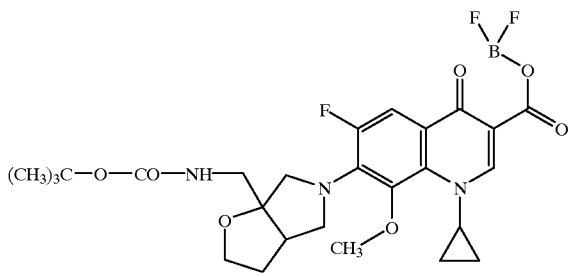

A.

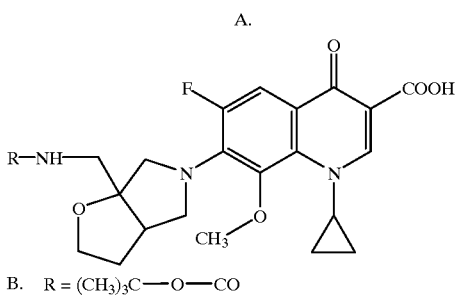

B. R = (CH₃)₃C—O—CO
C. R = H x CF₃COOH

A: 172 mg (0.5 mmol) of 1-cyclopropyl-6,7-difluoro-1,4-dihydro-8-methoxy-4-oxo-3-quinolinecarboxylic acid-BF₂-chelate in 5 ml of acetonitrile/dimethylformamide (1:1) are admixed with 150 mg (0.62 mmol) of 1-tert-butoxycarbonylaminomethyl-2-oxa-7-aza-bicylco[3.3.0]octane and 40 mg (0.38 mmol) of 1,4-diazabicyclo[2.2.2]octane and heated at 40° C. for 12 hours. The mixture is concentrated and can be used as crude product in step B. However, it can also be purified chromatographically over silica gel (mobile phase: dichloromethane/methanol 95:5) to characterize the intermediate step. This gives 128 mg of 7-(1-tert-butoxycarbonylaminomethyl-2-oxa-7-aza-bicyclo[3.3.0]oct-7-yl)-1-cyclopropyl-6-fluoro-1,4-dihydro-8-methoxy-4-oxo-3-quinolinecarboxylic acid-BF₂-chelate as a yellow solid; FAB-MS: m/e 566 [(M+H)⁺], 546 [(M–F⁻)⁺].

B: The evaporation residue obtained from step A is taken up in 20 ml of dichloromethane/methanol (1:1) and, after addition of 2.6 ml of triethylamine, heated under reflux for 10 hours. The mixture is concentrated and the residue is taken up in 4 ml of water and admixed with 3 ml of 2N HCl. The precipitate is filtered off with suction, washed with 20 ml of water and dried at 80° C. under high vacuum. This gives 210 mg of 7-(1-tert-butoxycarbonylaminomethyl-2-oxa-7-aza-bicyclo[3.3.0]oct-7-yl)-1-cyclopropyl-6-fluoro-1,4-dihydro-8-methoxy-4-oxo-3-quinoline-carboxylic acid;

$^1$H-NMR (400 MHz; DMSO): δ3.63 ppm s (OCH$_3$).

C: 206 mg (0.4 mmol) of the product from step B are dissolved in 13 ml of dichloromethane and admixed with 3.4 ml of trifluoroacetic acid. The solution is stirred at 25° C. for 30 minutes and then concentrated under reduced pressure. The residue is stirred repeatedly with absolute ethanol and the precipitate is filtered off with suction, washed well with ethanol and dried at 80° C. under high vacuum.

Yield: 114 mg (54% of theory) of 7-(1-aminomethyl-2-oxa-7-aza-bicyclo[3.3.0]oct-7-yl)-1-cyclopropyl-6-fluoro-1,4-dihydro-8-methoxy-4-oxo-3-quinolinecarboxylic acid trifluoroacetate, Melting point: 215–216° C. (decomposition).

Example 7

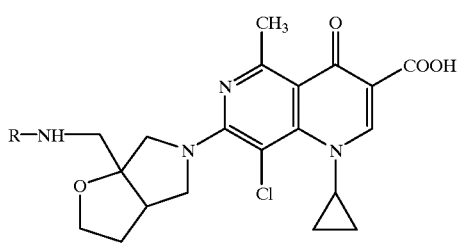

A. R = (CH$_3$)$_3$C—O—CO
B. R = H x CF$_3$COOH

A: 313 mg (1 mmol) of 7,8-dichloro-1-cyclopropyl-1,4-dihydro-5-methyl-4-oxo-1,6-naphthyridine-3-carboxylic acid in 5 ml of acetonitrile are admixed with 168 mg (1.5 mmol) of 1,4-diazabicyclo[2.2.2]octane and 266 mg (1.1 mmol) of 1-tert-butoxycarbonylaminomethyl-2-oxa-7-aza-bicyclo[3.3.0]octane and stirred at 50° C. for 2 hours. The mixture is concentrated, the residue is treated with water, and the precipitate is filtered off with suction, washed with water and dried at 90° C. under high vacuum.

Yield: 272 mg (52.5% of theory) of 7-(1-tert-butoxycarbonylaminomethyl-2-oxa-7-aza-bicyclo[3.3.0]oct-7-yl)-8-chloro-1-cyclopropyl-1,4-dihydro-5-methyl-4-oxo-1,6-naphthyridine-3-carboxylic acid, Melting point: 209–210° C. (decomposition).

B: 150 mg (0.29 mmol) of the product from step A in 2 ml of dichloromethane are admixed with 1.5 ml of trifluoroacetic acid and stirred at 25° C. for 45 minutes. The solution is concentrated and the residue is repeatedly admixed with dichloromethane and reconcentrated. The resulting salt is isolated and dried at 70° C. under high vacuum.

Yield: 68 mg (45% of theory) of 7-(1-aminomethyl-2-oxa-7-aza-bicyclo[3.3.0]oct-7-yl)-8-chloro-1-cyclopropyl-1,4-dihydro-5-methyl-4-oxo-1,6-naphthyridine-3-carboxylic acid trifluoroacetate, Melting point: 125–128° C. (decomposition).

Mass spectrum (ESI): m/e 419 [(M+H)$^+$].

Example 8

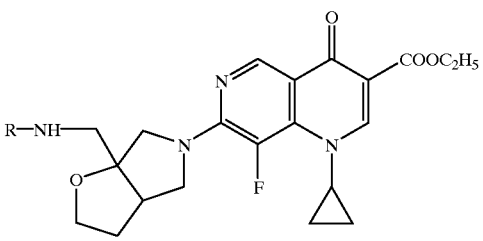

A. R = (CH$_3$)$_3$C—O—CO
B. R = H x CF$_3$COOH

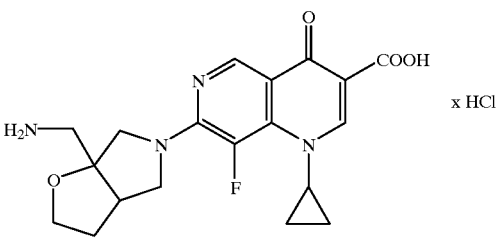

C.

A: By the method of Example 7A, ethyl 7-chloro-1-cyclopropyl-8-fluoro-1,4-dihydro-4-oxo-1,6-naphthyridine-3-carboxylate are converted, in a yield of 20%, into ethyl 7-(1-tert-butoxycarbonylaminomethyl-2-oxa-7-aza-bicyclo[3.3.0]oct-7-yl)-1-cyclopropyl-8-fluoro-1,4-dihydro-4-oxo-1,6-naphthyridine-3-carboxylate of melting point 146–148° C. (decomposition).

B: By the method of Example 7B, the product from step A is reacted with trifluoroacetic acid to give ethyl 7-(1-aminomethyl-2-oxa-7-aza-bicyclo[3.3.0]oct-7-yl)-1-cyclopropyl-8-fluoro-1,4-dihydro-4-oxo-1,6-naphthyridine-3-carboxylate trifluoroacetate of melting point 199–200° C. (decomposition).

C: 136 mg (0.25 mmol) of the product from step B are admixed with 10 ml of half-concentrated hydrochloric acid and heated under reflux for approximately 30 minutes. The mixture is concentrated and the residue is treated with ethanol. The solid is filtered off with suction and dried at 80° C. under high vacuum.

Yield: 97 mg (91% of theory) of 7-(1-aminomethyl-2-oxa-7-aza-bicyclo[3.3.0]oct-7-yl)-1-cyclopropyl-8-fluoro-1,4-dihydro-4-oxo-1,6-naphthyridine-3-carboxylic acid hydrochloride, Melting point: 301–304° C. (decomposition).

Example 9

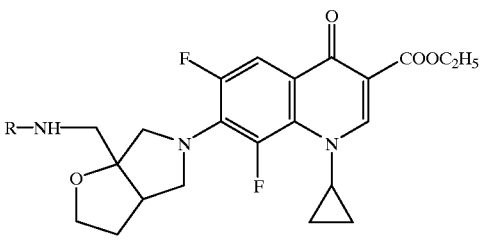

A. R = (CH$_3$)$_3$C—O—CO
B. R = H x CF$_3$COOH

A: By the method of Example 1A, ethyl 1-cyclopropyl-6,7,8-trifluoro-1,4-dihydro-4-oxo-3-quinolinecarboxylate is converted into ethyl 7-(1-tert-butoxycarbonylaminomethyl-2-oxa-7-aza-bicyclo[3.3.0]oct-7-yl)-1-cyclopropyl-6,8-difluoro-1,4-dihydro-4-oxo-3-quinolinecarboxylate.

B: 1.2 g of the product from step A in 10 ml of trifluoroacetic acid are stirred at 25° C. for 5 minutes and then concentrated, and the residue is stirred with ether. The resulting solid is purified chromatographically in dichloromethane/methanol (95:5) over a little silica gel.

Yield: 215 mg (17% of theory) of ethyl 7-(1-aminomethyl-2-oxa-7-aza-bicyclo[3.3.0]oct-7-yl)-1-cyclopropyl-6,8-difluoro-1,4-dihydro-4-oxo-3-quinolinecarboxylate trifluoroacetate, Melting point: 139–141° C.

Example 10

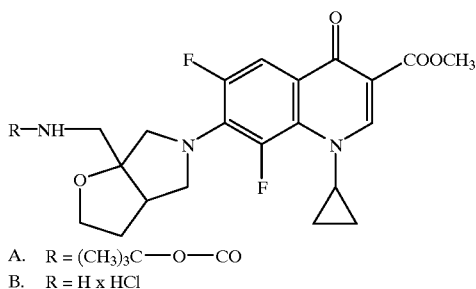

A.  R = (CH₃)₃C—O—CO
B.  R = H x HCl

A: 4.96 g (10 mmol) of 7-(1-tert-butoxycarbonylaminomethyl-2-oxa-7-aza-bicyclo[3.3.0]oct-7-yl)-1-cyclopropyl-6,8-difluoro-1,4-dihydro-4-oxo-3-quinolinecarboxylic acid are suspended in 200 ml of tetrahydrofuran/water (1:1) at 25° C., admixed with 2.3 g (7 mmol) of caesium carbonate and treated in an ultrasonic bath for approximately 10 minutes, resulting in a clear solution. At 30° C./15 mbar, most of the mixture is evaporated and the remaining solution is lyophilized. This gives 7.4 g of a colourless residue which mainly comprises the caesium salt of 7-(1-tert-butoxycarbonylaminomethyl-2-oxa-7-aza-bicyclo[3.3.0]oct-7-yl)-1-cyclopropyl-6,8-difluoro-1,4-dihydro-4-oxo-3-quinolinecarboxylic acid which is contaminated by some inorganic salt. 637 mg of this caesium salt are dissolved in 5 ml of dimethylformamide at 25° C. and admixed with 213 mg (1.5 mmol) of methyl iodide. The suspension is stirred at 25° C. overnight and then concentrated on a rotary evaporator and the residue is treated with light naphtha and dried at 80° C. under high vacuum.

Yield: 360 mg of methyl 7-(1-tert-butoxycarbonylaminomethyl-2-oxa-7-aza-bicyclo[3.3.0]oct-7-yl)-1-cyclopropyl-6,8-difluoro-1,4-dihydro-4-oxo-3-quinolinecarboxylate, Melting point: 141–144° C. (decomposition).

B: The product obtained from step A is dissolved in 25 ml of dichloromethane, admixed with 1.5 ml of trifluoroacetic acid and stirred at room temperature for 2 hours. The solution is concentrated under reduced pressure and the residue is purified chromatographically over silica gel using dichloromethane/methanol/17% ammonia=150:20:1. The resulting product is initially charged in 2 ml of water and dissolved with 0.76 ml of 1N HCl. The mixture is concentrated at 60° C./15 mbar and the salt is dried at 50° C. under high vacuum.

Yield: 226 mg of methyl 7-(1-aminomethyl-2-oxa-7-aza-bicyclo[3.3.0]oct-7-yl)-1-cyclopropyl-6,8-difluoro-1,4-dihydro-4-oxo-3-quinolinecarboxylate hydrochloride, Melting point: 109–111° C.

Example 11

A: By the method of Example 10A, 1-bromobutane gives 1-butyl 7-(1-tert-butoxycarbonylaminomethyl-2-oxa-7-aza-bicyclo[3.3.0]oct-7-yl)-1-cyclopropyl-6,8-difluoro-1,4-dihydro-4-oxo-3-quinolinecarboxylate of melting point 146–148° C.

B: By the method of Example 10B, the protecting group is cleaved off with trifluoroacetic acid and the resulting trifluoroacetate is purified chromatographically using the ammoniacal mobile phase. 1-Butyl 7-(1-aminomethyl-2-oxa-7-aza-bicyclo[3.3.0]oct-7-yl)-1-cyclopropyl-6,8-difluoro-1,4-dihydro-4-oxo-3-quinolinecarboxylate of melting point 117–119° C. (decomposition) is isolated.

Example 12

A: By the method of Example 10A, allyl bromide gives allyl 7-(1-tert-butoxycarbonylaminomethyl-2-oxa-7-aza-bicyclo[3.3.0]oct-7-yl)-1-cyclopropyl-6,8-difluoro-1,4-dihydro-4-oxo-3-quinolinecarboxylate of melting point 143–145° C.

B: By the method of Example 10B, the protecting group is cleaved off with trifluoroacetic acid and the resulting trifluoroacetate is purified chromatographically using the ammoniacal mobile phase. Allyl 7-(1-aminomethyl-2-oxa-7-aza-bicyclo[3.3.0]oct-7-yl)-1-cyclopropyl-6,8-difluoro-1,4-dihydro-4-oxo-3-quinolinecarboxylate of melting point 133–135° C. (decomposition) is isolated.

C: By the method of Example 10B, the protecting group is cleaved off with trifluoroacetic acid and the resulting crude trifluoroacetate is treated with ethanol and ether and isolated as a solid: allyl 7-(1-aminomethyl-2-oxa-7-aza-bicyclo[3.3.0]oct-7-yl)-1-cyclopropyl-6,8-difluoro-1,4-dihydro-4-oxo-3-quinolinecarboxylate trifluoroacetate of melting point 118–119° C. (decomposition).

Example 13

A: By the method of Example 10A, propargyl bromide gives propargyl 7-(1-tert-butoxycarbonylaminomethyl-2-oxa-7-aza-bicyclo[3.3.0]oct-7-yl)-1-cyclopropyl-6,8-difluoro-1,4-dihydro-4-oxo-3-quinolinecarboxylate of melting point 159–160° C.

B: By the method of Example 10B, the protecting group is cleaved off with trifluoroacetic acid and the resulting trifluoroacetate is purified chromatographically using the ammoniacal mobile phase. Propargyl 7-(1-aminomethyl-2-oxa-7-aza-bicyclo[3.3.0]oct-7-yl)-1-cyclopropyl-6,8-difluoro-1,4-dihydro-4-oxo-3-quinolinecarboxylate of melting point 127–129° C. (decomposition) is isolated.

Example 14

A: By the method of Example 10A, benzyl bromide gives benzyl 7-(1-tert-butoxycarbonylaminomethyl-2-oxa-7-aza-bicyclo[3.3.0]oct-7-yl)-1-cyclopropyl-6,8-difluoro-1,4-dihydro-4-oxo-3-quinolinecarboxylate of melting point 148–149° C.

B: By the method of Example 10B, the protecting group is cleaved off with trifluoroacetic acid and the resulting trifluoroacetate is purified chromatographically using the ammoniacal mobile phase. Benzyl 7-(1-aminomethyl-2-oxa-7-aza-bicyclo[3.3.0]oct-7-yl)-1-cyclopropyl-6,8-difluoro-1,4-dihydro-4-oxo-3-quinolinecarboxylate of melting point 118–119° C. (decomposition) is isolated.

C: By the method of Example 10B, the protecting group is cleaved off with trifluoroacetic acid and the resulting crude trifluoroacetate is treated with ethanol and ether and isolated as a solid: benzyl 7-(1-aminomethyl-2-oxa-7-aza-bicyclo[3.3.0]oct-7-yl)-1-cyclopropyl-6,8-difluoro-1,4-dihydro-4-oxo-3-quinolinecarboxylate trifluoroacetate of melting point 119–120° C. (decomposition).

Example 15

A: By the method of Example 10A, ethyl bromoacetate gives ethoxycarbonylmethyl 7-(1-tert-butoxycarbonylaminomethyl-2-oxa-7-aza-bicyclo[3.3.0]oct-7-yl)-1-cyclopropyl-6,8-difluoro-1,4-dihydro-4-oxo-3-quinolinecarboxylate of melting point 150–152° C.

B: By the method of Example 10B, the protecting group is cleaved off with trifluoroacetic acid and the resulting trifluoroacetate is purified chromatographically using the ammoniacal mobile phase. Ethoxycarbonylmethyl 7-(1-aminomethyl-2-oxa-7-aza-bicyclo[3.3.0]oct-7-yl)-1-cyclopropyl-6,8-difluoro-1,4-dihydro-4-oxo-3-quinolinecarboxylate of melting point 144–146° C. (decomposition) is isolated.

Example 16

A. R = (CH₃)₃C—O—CO
B. R = H x HCl

A: By the method of Example 1A, 1-(cis-2-fluoro-cyclopropyl)-6,7-difluoro-1,4-dihydro-4-oxo-3-quinolinecarboxylic acid is converted into 7-(1-tert-butoxycarbonylaminomethyl-2-oxa-7-aza-bicyclo[3.3.0]oct-7-yl)-1-(cis-2-fluorocyclopropyl)-6-fluoro-1,4-dihydro-4-oxo-3-quinolinecarboxylic acid (74% of theory) of melting point 202–206° C. (decomposition).

B: By the method of Example 1B, the product from step A is reacted with half-concentrated hydrochloric acid to give 7-(1-aminomethyl-2-oxa-7-aza-bicyclo[3.3.0]oct-7-yl)-1-(cis-2-fluoro-cyclopropyl-6-fluoro-1,4-dihydro-4-oxo-3-quinolinecarboxylic acid hydrochloride of melting point 257–259° C. (decomposition).

Example 17

A. R = (CH₃)₃C—O—CO
B. R = H

A: By the method of Example 1A, 1-tert-butyl-6,7-difluoro-1,4-dihydro-4-oxo-3-quinolinecarboxylic acid is converted into 7-(1-tert-butoxycarbonylaminomethyl-2-oxa-7-aza-bicyclo[3.3.0]oct-7-yl)-1-tert-butyl-6-fluoro-1,4-dihydro-4-oxo-3-quinolinecarboxylic acid (84% of theory) of melting point 131–133° C. (decomposition).

B: By the method of Example 1B, the product from step A is deblocked with half-concentrated hydrochloric acid for 15 minutes and the resulting crude product is purified chromatographically over silica gel using an ammoniacal mobile phase (dichloromethane/methanol/17% ammonia 30:8:1). In addition to 7-(1-aminomethyl-2-oxa-7-aza-bicyclo[3.3.0]oct-7-yl)-6-fluoro-1,4-dihydro-4-oxo-3-quinolinecarboxylic acid (melting point: >330° C.), this gives 7-(1-aminomethyl-2-oxa-7-aza-bicyclo[3.3.0]oct-7-yl)-1-tert-butyl-6-fluoro-1,4-dihydro-4-oxo-3-quinolinecarboxylic acid of melting point 217–218° C. (decomposition).

Example 18

A. R = (CH₃)₃C—O—CO
B. R = H x CF₃COOH

A: By the method of Example 1A, 1-(fluoro-tert-butyl)-6,7-difluoro-1,4-dihydro-4-oxo-3-quinolinecarboxylic acid is converted into 7-(1-tert-butoxycarbonylaminomethyl-2-oxa-7-aza-bicyclo[3.3.0]oct-7-yl)-1-(fluoro-tert-butyl)-6-fluoro-1,4-dihydro-4-oxo-3-quinolinecarboxylic acid (81% of theory) of melting point 161–162° C. (decomposition).

B: By the method of Example 1B, the product from step A is deblocked with trifluoroacetic acid and the crude product which is obtained after concentration is crystallized by treatment with ethanol. This gives 7-(1-aminomethyl-2-oxa-7-aza-bicyclo[3.3.0]oct-7-yl)-1-(fluoro-tert-butyl)-6-fluoro-1,4-dihydro-4-oxo-3-quinolinecarboxylic acid trifluoroacetate of melting point 197–198° C. (decomposition).

Example 19

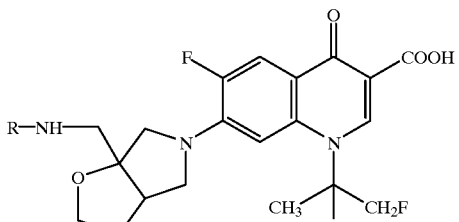

A. R = (CH$_3$)$_3$C—O—CO
B. R = H x CF$_3$COOH

A: By the method of Example 1A, 1-(difluoro-tert-butyl)-6,7-difluoro-1,4-dihydro-4-oxo-3-quinolinecarboxylic acid is converted into 7-(1-tert-butoxycarbonylaminomethyl-2-oxa-7-aza-bicyclo[3.3.0]oct-7-yl)-1-(difluoro-tert-butyl)-6-fluoro-1,4-dihydro-4-oxo-3-quinolinecarboxylic acid (59% of theory).

B: By the method of Example 6C, the product from step A is deblocked with trifluoroacetic acid in dichloromethane, the crude product which is obtained after concentration is taken up in water and washed with dichloromethane and the aqueous phase is lyophilized. This gives, in a yield of 12%, 7-(1-aminomethyl-2-oxa-7-aza-bicyclo[3.3.0]oct-7-yl)-1-(difluoro-tert-butyl)-6-fluoro-1,4-dihydro-4-oxo-3-quinolinecarboxylic acid trifluoroacetate of melting point 154–160° C. (decomposition).

Example 20

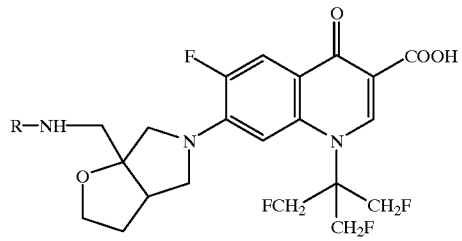

A. R = (CH$_3$)$_3$C—O—CO
B. R = H x HCl

A: By the method of Example 1A, 1-(trifluoro-tert-butyl)-6,7-difluoro-1,4-dihydro-4-oxo-3-quinolinecarboxylic acid is converted into 7-(1-tert-butoxycarbonylaminomethyl-2-oxa-7-aza-bicyclo[3.3.0]oct-7-yl)-1-(trifluoro-tert-butyl)-6-fluoro-1,4-dihydro-4-oxo-3-quinolinecarboxylic acid (73% of theory) of melting point 131° C.

B: By the method of Example 1B, the product from step A is deblocked with hydrochloric acid. This gives, in a yield of 41%, 7-(1-aminomethyl-2-oxa-7-aza-bicyclo[3.3.0]oct-7-yl)-1-(trifluoro-tert-butyl)-6-fluoro-1,4-dihydro-4-oxo-3-quinolinecarboxylic acid hydrochloride of melting point 228° C. (decomposition).

Example 21

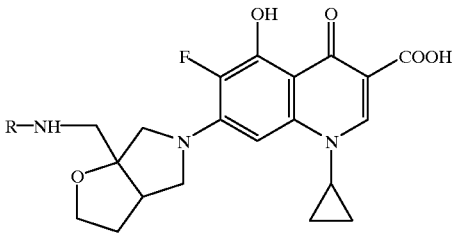

A. R = (CH$_3$)$_3$C—O—CO
B. R = H x HCl

A: By the method of Example 1A, 1-cyclopropyl-6,7-difluoro-5-hydroxy-1,4-dihydro-4-oxo-3-quinolinecarboxylic acid is converted into 7-(1-tert-butoxycarbonylaminomethyl-2-oxa-7-aza-bicyclo[3.3.0]oct-7-yl)-1-cyclopropyl-6-fluoro-5-hydroxy-1,4-dihydro-4-oxo-3-quinolinecarboxylic acid (63% of theory).

B: By the method of Example 1B, the product from step A is reacted with half-concentrated hydrochloric acid to give 7-(1-aminomethyl-2-oxa-7-aza-bicyclo[3.3.0]oct-7-yl)-1-cyclopropyl-6-fluoro-5-hydroxy-1,4-dihydro-4-oxo-3-quinolinecarboxylic acid hydrochloride of melting point 225° C. (decomposition).

Example 22

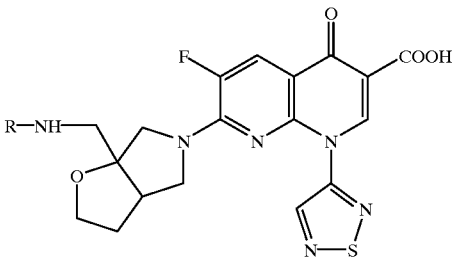

A. R = (CH$_3$)$_3$C—O—CO
B. R = H x HCl

A: By the method of Example 1A, 7-chloro-6-fluoro-1,4-dihydro-4-oxo-1-(1,2,5-thiadiazol-3-yl)-1,8-naphthyridine-3-carboxylic acid is converted into 7-(1-tert-butoxycarbonylaminomethyl-2-oxa-7-aza-bicyclo[3.3.0]oct-7-yl)-6-fluoro-1,4-dihydro-4-oxo-1-(1,2,5-thiadiazol-3-yl)-1,8-naphthyridine-3-carboxylic acid (66% of theory).

B: By the method of Example 1B, the product from step A is reacted with half-concentrated hydrochloric acid to give 7-(1-aminomethyl-2-oxa-7-aza-bicyclo[3.3.0]oct-7-yl)-6-fluoro-1,4-dihydro-4-oxo-1-(1 ,2,5-thiadiazol-3-yl)-1,8-naphthyridine-3-carboxylic acid hydrochloride of melting point 207° C. (decomposition).

Example 23

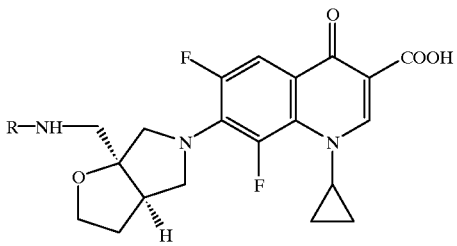

A. R = (CH₃)₃C—O—CO; (+)-enantiomer
B. R = H x HCl; (+)-enantiomer

A: A mixture of 481 mg (1.7 mmol) of 1-cyclopropyl-6,7,8-trifluoro-1,4-dihydro-4-oxo-3-quinolinecarboxylic acid in 5 ml of acetonitrile and 2.5 ml of dimethylformamide with 217 mg (1.9 mmol) of 1,4-diazabicyclo[2.2.2]octane and 467 mg (1.9 mmol) of (+)-(1R,5R)-1-tert-butoxycarbonylaminomethyl-2-oxa-7-aza-bicyclo[3.3.0]octane is heated under reflux for 5 hours, and the solution is filtered hot. The reaction product crystallizes out and is filtered off with suction and washed with a little acetonitrile. The precipitate is subsequently stirred well with approximately 40 ml of water, filtered off with suction and dried at 80° C. under high vacuum.

Yield: 748 mg (87% of theory) of (+)-(1R,5R)-7-(1-tert-butoxycarbonylaminomethyl-2-oxa-7-aza-bicyclo[3.3.0]oct-7-yl)-1-cyclopropyl-6,8-difluoro-1,4-dihydro-4-oxo-3-quinolinecarboxylic acid, Melting point: 202–203° C. (decomposition).
[α]³: +94° (c=0.46, CHCl₃).

B: 701 mg (1.39 mmol) of (+)-(1R,5R)-7-(1-tert-butoxycarbonylaminomethyl-2-oxa-7-aza-bicyclo[3.3.0]oct-7-yl)-1-cyclopropyl-6,8-difluoro-1,4-dihydro-4-oxo-3-quinolinecarboxylic acid are dissolved in 16 ml of hot, half-concentrated hydrochloric acid and the solution is filtered and concentrated at 60° C./15 mbar. The residue is admixed with some ethanol and reconcentrated, and the salt is isolated and dried at 80° C. under high vacuum.

Yield: 537 mg (88% of theory) of (+)-(1S,5R)-7-(aminomethyl-2-oxa-7-aza-bicyclo[3.3.0]oct-7-yl)-1-cyclopropyl-6,8-difluoro-1,4-dihydro-4-oxo-3-quinolinecarboxylic acid hydrochloride, Melting point: 214–216° C. (decomposition).
[α]³: +49° (c=0.45, DMF).
ee>99.8% (determined by capillary electrophoresis).

Example 24

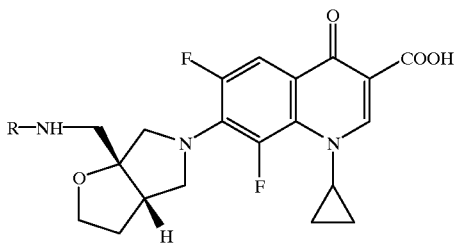

A. R = (CH₃)₃C—O—CO; (-)-enantiomer
B. R = H x HCl; (-)-enantiomer

A: By the method of Example 23 A, (-)-(1S,5S)-1-tert-butoxycarbonylaminomethyl-2-oxa-7-aza-bicyclo[3.3.0]octane gives, in a yield of 67%, (-)-(1S,5S)-7-(1-tert-butoxycarbonylaminomethyl-2-oxa-7-aza-bicyclo[3.3.0]oct-7-yl)-1-cyclopropyl-6,8-difluoro-1,4-dihydro-4-oxo-3-quinoline-carboxylic acid, Melting point: 209–210° C. (decomposition).
[α]³: -96° (c=0.43, CHCl₃).

B: By the method of Example 23 B, the product from step A is deblocked by reaction with hydrochloric acid to give (-)-(1RS,5S)-7-(aminomethyl-2-oxa-7-aza-bicyclo[3.3.0]oct-7-yl)-1-cyclopropyl-6,8-difluoro-1,4-dihydro-4-oxo-3-quinolinecarboxylic acid hydrochloride, Melting point: 214–216° C. (decomposition).
[α]³: -49° (c=0.33, DMF).
ee>99.8% (determined by capillary electrophoresis).

Example 25

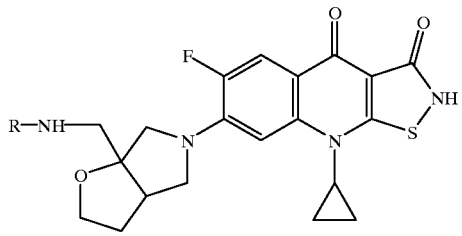

A. R = (CH₃)₃C—O—CO
B. R = H x CF₃COOH

A: 250 mg (0.85 mmol) of 9-cyclopropyl-6,7-difluoro-2,3,4,9-tetrahydroisothiazolo[5,4-b]quinoline-3,4-dione in 10 ml of absolute pyridine and 247 mg (1.02 mmol) of 1-tert-butoxycarbonylaminomethyl-2-oxa-7-aza-bicyclo[3.3.0]octane are heated under reflux overnight. After cooling, the mixture is admixed with 40 ml of water and the precipitate is filtered off with suction, washed with water and dried under reduced pressure. This gives 190mg of 7-(1-tert-butoxycarbonylaminomethyl-2-oxa-7-aza-bicyclo[3.3.0]oct-7-yl)-9-cyclopropyl-6-fluoro-2,3,4,9-tetrahydroisothiazolo[5,4-b]quinoline-3,4-dione.

B: The product from step A is, by the method of Example 6C, deblocked with trifluoroacetic acid in dichloromethane, the solution is concentrated and evaporated repeatedly with a little toluene, the residue is taken up in 5 ml of methanol and the salt is precipitated out using 20 ml of isopropanol.

Yield: 163 mg of 7-(1-aminomethyl-2-oxa-7-aza-bicyclo[3.3.0]oct-7-yl)-9-cyclopropyl-6-fluoro-2,3,4,9-tetrahydroisothiazolo[5,4-b]quinoline-3,4-dione trifluoroacetate, Melting point: 215° C. (decomposition).

Example 26

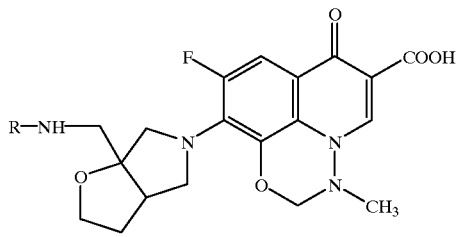

-continued

A.  R = (CH₃)₃C—O—CO
B.  R = H x HCl

A: 0.72 g (2.72 mmol) of 9,10-difluoro-3-methyl-7-oxo-2,3-dihydro-7H-pyrido[1,2,3-de][1,3,4]-benzoxadiazine-6-carboxylic acid in 36 ml of acetonitrile is admixed with 0.4 g (2.8 mmol) of 1-tert-butoxycarbonylaminomethyl-2-oxa-7-aza-bicyclo[3.3.0]octane and 0.6 g of 1,4-diazabicyclo[2.2.2]octane and the mixture is heated under reflux for 16 hours. The mixture is concentrated and the residue is taken up in water and extracted with dichloromethane. The extract is then dried with sodium sulphate and concentrated, the residue is stirred with methanol and the resulting solid is isolated and dried under reduced pressure. This gives 0.6 g of 10-(1-tert-butoxycarbonylaminomethyl-2-oxa-7-aza-bicyclo[3.3.0]oct-7-yl)-9-fluoro-3-methyl-7-oxo-2,3-dihydro-7H-pyrido[1,2,3-de][1,3,4]-benzoxadiazine-6-carboxylic acid of melting point 176° C.

B: 0.6 g (1.9 mmol) of the product from step A is dissolved in 105 ml of 4N hydrochloric acid/dioxane (1:1) and heated at 60° C. for 2 hours. The solution is concentrated and stirred with some ethanol and the precipitate is filtered off with suction and dried.

Yield: 110 mg of 10-(1-aminomethyl-2-oxa-7-aza-bicyclo[3.3.0]oct-7-yl)-9-fluoro-3-methyl-7-oxo-2,3-dihydro-7H-pyrido[1,2,3-de][1,3,4]-benzoxadiazine-6-carboxylic acid hydrochloride, Melting point: 233° C.

Example 27

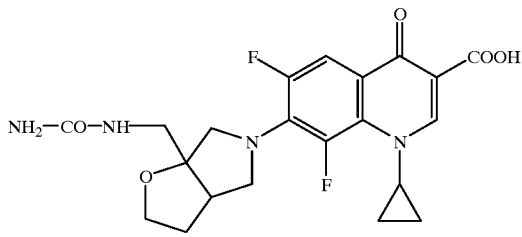

A mixture of 283 mg (1 mmol) of 1-cyclopropyl-6,7,8-trifluoro-1,4-dihydro4-oxo-3-quinolinecarboxylic acid in 4 ml of acetonitrile and 2 ml of dimethylformamide and 112 mg (1 mmol) of 1,4-diazabicyclo[2.2.2]octane and 234 mg (1.3 mmol) of 1-ureidomethyl-2-oxa-7-aza-bicyclo[3.3.0]octane is heated under reflux for 2 hours. The mixture is concentrated and the residue is admixed with some water and treated in an ultrasonic bath. The undissolved precipitate is filtered off with suction, washed with water and dried at 100° C. under high vacuum.

Yield: 237 mg (53% of theory) of 1-cyclopropyl-6,8-difluoro-1,4-dihydro-4-oxo-7-(1-ureidomethyl-2-oxa-7-aza-bicyclo[3.3.0]oct-7-yl)-3-quinolinecarboxylic acid, Melting point: 185–187° C. (decomposition).

Example 28

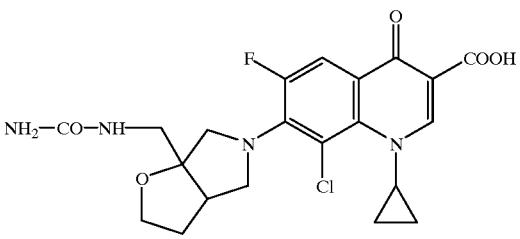

By the method of Example 27, 8-chloro-1-cyclopropyl-6-fluoro-1,4-dihydro-4-oxo-7-(1-ureidomethyl-2-oxa-7-aza-bicyclo[3.3.0]oct-7-yl)-3-quinolinecarboxylic acid is obtained, Melting point: 232–234° C. (decomposition).

Example 29

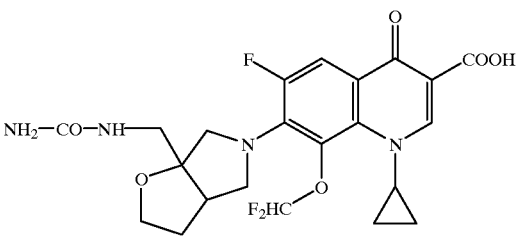

By the method of Example 27, 1-cyclopropyl-8-difluoromethoxy-6-fluoro-1,4-dihydro-4-oxo-7-(1-ureidomethyl-2-oxa-7-aza-bicyclo[3.3.0]oct-7-yl)-3-quinolinecarboxylic acid is obtained, Melting point: 232–234° C. (decomposition).

Example 30

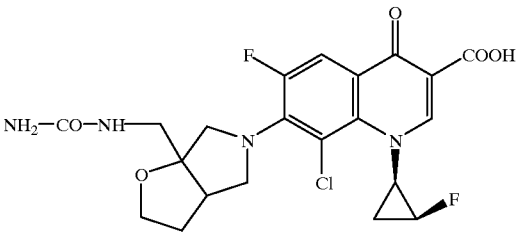

By the method of Example 27, 8-chloro-6-fluoro-1-[(1R,2S)-2-fluoro-cyclopropyl]-1,4-dihydro-4-oxo-7-(1-ureidomethyl-2-oxa-7-aza-bicyclo[3.3.0]oct-7-yl)-3-quinolinecarboxylic acid is obtained, Melting point: 208–210° C. (decomposition).

Example 31

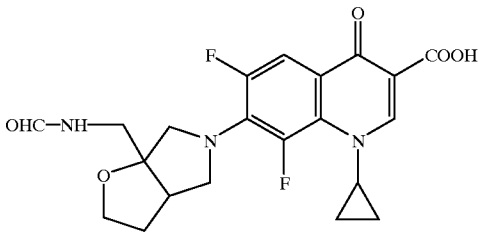

310 mg (1 mmol) of 7-(1-aminomethyl-2-oxa-7-aza-bicyclo[3.3.0]oct-7-yl)-1-cyclopropyl-6,8-difluoro-1,4-dihydro-4-oxo-3-quinolinecarboxylic acid in 2.3 ml of dimethylformamide is heated under reflux with 2.3 ml of formic acid for 8 hours. The mixture is concentrated under reduced pressure, the residue is stirred with 8 ml of water and the precipitate is filtered off with suction, dried and chromatographed over silica gel using dichloromethane/methanol (95:5) as mobile phase.

Yield: 173 mg (40% of theory) of 1-cyclopropyl-6,8-difluoro-7-(1-formylaminomethyl-2-oxa-7-aza-bicyclo[3.3.0]oct-7-yl)-1,4-dihydro4-oxo-3-quinolinecarboxylic acid, Melting point: 208–209° C. (decomposition), Example 32

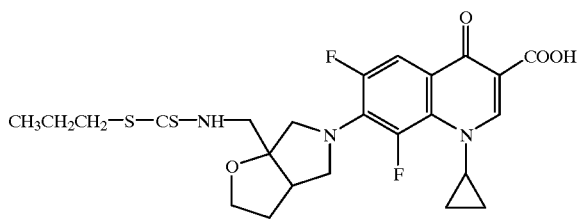

730 mg (2 mmol) of 7-(1-aminomethyl-2-oxa-7-aza-bicyclo[3.3.0]oct-7-yl)-1-cyclopropyl-6,8-difluoro-1,4-dihydro-4-oxo-3-quinolinecarboxylic acid are initially charged at room temperature in a mixture of 1.3 ml of water and 1 ml of 4N aqueous sodium hydroxide solution, and the mixture is cooled with ice and admixed with 0.24 ml of carbon disulphide. The mixture is stirred at 5° C. for 1 hour and subsequently at room temperature for another 15 hours. The suspension is admixed with 50 ml of acetone and cooled, and the precipitate is filtered off with suction, washed with acetone and dried at 80° C. under high vacuum. This gives 657 mg of the sodium salt of the dithiourethane. 409 mg of this sodium salt are initially charged in 5 ml of dimethylformamide and admixed with 123 mg of 1-bromopropane in 1 ml of dimethylformamide, and the mixture is stirred at room temperature overnight. The mixture is concentrated at 70° C./12 mbar, the residue is stirred with ethanol, the precipitate is filtered off with suction and dried and the resulting crude product (225 mg) is purified by chromatography over silica gel using dichloromethane/methanol/17% ammonia (150:4:1).

Yield: 56 mg of 7-(1-propylthio-thiocarbonylaminomethyl-2-oxa-7-aza-bicyclo[3.3.0]oct-7-yl)-1-cyclopropyl-6,8-difluoro-1,4-dihydro-4-oxo-3-quinolinecarboxylic acid, Melting point: 162–166° C. (decomposition).

Example 33

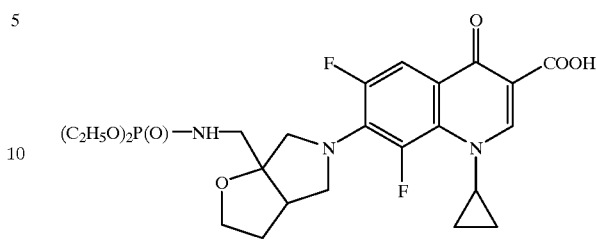

395 mg (1 mmol) of 7-(1-aminomethyl-2-oxa-7-aza-bicyclo[3.3.0]oct-7-yl)-1-cyclopropyl-6,8-difluoro-1,4-dihydro-4-oxo-3-quinolinecarboxylic acid in 15 ml of dichloromethane are admixed with 406 mg (2 mmol) of bis(trimethylsilyl)acetamide and stirred at 25° C. for 3 hours. The mixture is subsequently admixed with 173 mg (1 mol) of diethylphosphoryl chloride and stirred at room temperature for 24 hours. Unreacted starting material is filtered off with suction, the mother liquor is concentrated and the residue is chromatographed over silica gel (mobile phase: dichloromethane/methanol 95:5).

Yield: 73 mg (1.5%) of 7-(1-diethoxyphosphoryl-aminomethyl-2-oxa-7-aza-bicyclo[3.3.0]oct-7-yl)-1-cyclopropyl-6,8-difluoro-1,4-dihydro-4-oxo-3-quinolinecarboxylic acid, FAB-MS: m/e 542 [(M+H)$^+$], 524.

Example 34

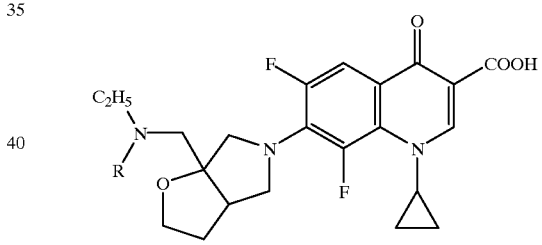

A.  R = (CH$_3$)$_3$C—O—CO
B.  R = H x HCl

A: A mixture of 283 mg (1 mmol) of 1-cyclopropyl-6,7,8-trifluoro-1,4-dihydro-4-oxo-3-quinolinecarboxylic acid in 3 ml of acetonitrile and 1.5 ml of dimethylformamide and 120 mg (1.07 mmol) of 1,4-diazabicyclo[2.2.2]octane and 400 mg of (1.5 mmol) of 1-(N-tert-butoxycarbonyl-N-ethyl-aminomethyl)-2-oxa-7-aza-bicyclo[3.3.0]octane is heated under reflux for 6 hours, the solution is concentrated, and the residue is admixed with 20 ml of water and treated in an ultrasonic bath. The undissolved precipitate is filtered off with suction, washed with water and dried at 80° C. under high vacuum.

Yield: 460 mg (86% of theory) of 7-[1-(N-tert-butoxycarbonyl-N-ethylaminomethyl)-2-oxa-7-aza-bicyclo[3.3.0]oct-7-yl]-1-cyclopropyl-6,8-difluoro-1,4-dihydro-4-oxo-3-quinolinecarboxylic acid, Melting point: 166–168° C. (decomposition).

B: 430 mg (0.8 mmol) of the product from step A are dissolved in 15 ml of hot, half-concentrated hydrochloric acid, and the solution is filtered and concentrated at 60°

C./15 mbar. The residue is admixed with some ethanol and reconcentrated, and the salt is isolated and dried at 80° C. under high vacuum.

Yield: 272 mg (72% of theory) of 7-(ethylaminomethyl-2-oxa-7-aza-bicyclo[3.3.0]oct-7-yl)-1-cyclopropyl-6,8-difluoro-1,4-dihydro-4-oxo-3-quinolinecarboxylic acid hydrochloride, Melting point: 280–281° C. (decomposition).

Example 35

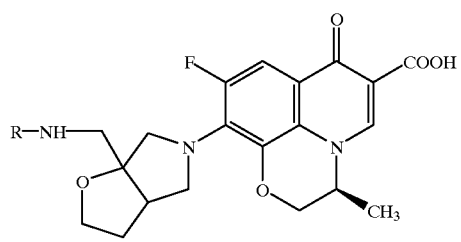

A.  R = (CH$_3$)$_3$C——O——CO
B.  R = H x HCl

A: By the method of Example 1A, 9,10-difluoro-3(S)-methyl-7-oxo-2,3-dihydro-7H-pyrido[1,2,3-de][1,4]benzoxazine-6-carboxylic acid is converted into 10-(1-tert-butoxycarbonylaminomethyl-2-oxa-7-aza-bicyclo[3.3.0]oct-7-yl)-9-fluoro-3(S)-methyl-7-oxo-2,3-dihydro-7H-pyrido[1,2,3-de][1,4]benzoxazine-6-carboxylic acid of melting point 157–158° C. (decomposition).

B: By the method of Example 1B, the product from step A is reacted with half-concentrated hydrochloric acid to give 10-(1-aminomethyl-2-oxa-7-aza-bicyclo[3.3.0]oct-7-yl)-9-fluoro-3(S)-methyl-7-oxo-2,3-dihydro-7H-pyridol[1,2,3-de][1,4]benzoxazine-6-carboxylic acid hydrochloride of melting point 191–193° C. (decomposition).

Example 36

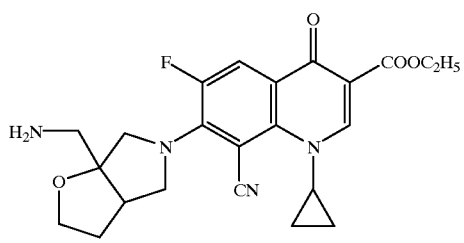

350 mg (1.21 mmol) of ethyl 8-cyano-1-cyclopropyl-6,7-difluoro-1,4-dihydro4-oxo-quinolinecarboxylate and 260 mg (1.2 mmol) of (1SR,5RS)-1-aminomethyl-2-oxa-7-azabicyclo[3.3.0]octane dihydrochloride in 30 ml of absolute acetonitrile are admixed with 470 mg (4.64 mmol) of triethylamine and stirred at room temperature overnight. The mixture is concentrated and the residue is purified chromatographically (silica gel; dichloromethane/methanol 9:1). 450 mg (86% of theory) of ethyl 7-([1SR,5RS]-1-aminomethyl-2-oxa-7-azabicyclo[3.3.0]oct-7-yl)-8-cyano-1-cyclopropyl-6-fluoro-1,4-dihydro-4-oxo-quinolinecarboxylate are isolated, melting point: 193° C.

Ethyl 7-([1R,5S]-1-aminomethyl-2-oxa-7-azabicyclo[3.3.0]oct-7-yl)-8-cyano-1-cyclopropyl-6-fluoro-1,4-dihydro-4-oxo-quinolinecarboxylate and 7-([1S,5R]-1-aminomethyl-2-oxa-7-azabicyclo[3.3.0]oct-7-yl)-8-cyano-1-cyclopropyl-6-fluoro-1,4-dihydro-4-oxo-quinolinecarboxylate are also prepared in a corresponding manner.

What is claimed is:

1. A diastereomerically pure or enantiomerically pure compound from the group consisting of
7-(1-aminomethyl-2-oxa-7-aza-bicyclo[3.3.0]oct-7-yl)-1-cyclopropyl-8-difluoromethoxy-6-fluoro-1,4-dihydro-4-oxo-3-quinolinecarboxylic acid, and
7-(1-aminomethyl-2-oxa-7-aza-bicyclo[3.3.0]oct-7-yl)-8-cyano-1-cyclopropyl-6-fluoro-1,4-dihydro-4-oxo-3-quinolinecarboxylic acid.

2. The compound (+)-7-[(1S,5R)-1-Aminomethyl-2-oxa-7-aza-bicyclo[3.3.0]oct-7-yl]-8-cyano-1-cyclopropyl-6-fluoro-1,4-dihydro-4-oxo-quinolinecarboxylic acid.

3. A pharmaceutical composition comprising the compound according to claim 2 and a pharmaceutical acceptable carrier.

4. A method of treating a *Heliobacter pylori* infection or a gastroduodenal disorder associated therewith, said method comprising administering to a patient in need thereof an effective amount therefor of at least one compound of the formula (I):

in which

Q represents a radical of the formulae

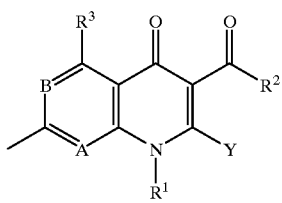

in which $R^1$ represents alkyl having 1 to 4 carbon atoms which is optionally mono- to trisubstituted by halogen or hydroxyl, alkenyl having 2 to 4 carbon atoms, cycloalkyl having 3 to 6 carbon atoms which is optionally substituted by 1 or 2 fluorine atoms, bicyclo[1.1.1]pent-1-yl, 1,1-dimethylpropargyl, 3-oxetanyl, methoxy, amino, methylamino, dimethylamino, phenyl which is optionally mono- or disubstituted by halogen, amino or hydroxyl, isoxazolyl, or thiadiazolyl;

$R^2$ represents hydroxyl, alkoxy having 1 to 4 carbon atoms which is optionally substituted by hydroxyl, methoxy, amino, dimethylamino or ethoxycarbonyl, benzyloxy, allyloxy, propargyloxy or (5-methyl-2-oxo-1,3-dioxol-4-yl)-methyloxy, acetoxymethyloxy, pivaloyloxymethyloxy, 5-indanyloxy, phthalidinyloxy, 3-acetoxy-2-oxo-butyloxy, nitromethyl or dialkoxycarbonylmethyl having 1 to 2 carbon atoms in each alkyl moiety;

$R^3$ represents hydrogen, amino, hydroxyl, or halogen;

A represents N or C—$R^7$ in which $R^7$ represents hydrogen, halogen, $CF_3$, $OCH_3$, $OCHF_2$, $CH_3$, CN, CH=$CH_2$ or C≡CH or else together with $R^1$ may form a bridge of the structure —*O—$CH_2$—CH—$CH_3$, —*S—$CH_2$—$CH_2$—, —*S—$CH_2$—CH—$CH_3$, —*$CH_2$—$CH_2$—CH—$CH_3$ or —*O—$CH_2$—N—$R^8$ where the atom marked with * is attached to the carbon atom of A and in which R$^8$ represents hydrogen, methyl or formyl;

B represents N, C—H, C—F, C—Cl, C—NO$_2$, C—NH$_2$;

Y represents hydrogen or together with R$^2$ may form a bridge of the structure —*S—NH— where the atom marked with * represents Y; and T represents a radical of the formula:

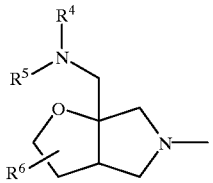

in which

R$^4$ represents H, CH$_3$, C$_2$H$_5$, optionally amino-substituted acyl having 1 to 5 carbon atoms, alkoxycarbonyl, aminocarbonyl, alkylthiothiocarbonyl and dialkoxyphosphoryl having 1 to 4 carbon atoms in the alkyl moiety;

R$^5$ represents H, CH$_3$ or C$_2$H$_5$; and

R$^6$ represents H or CH$_3$;

or a pharmaceutically useful hydrate, acid addition salt or alkali metal, alkaline earth metal, silver or guanidinium salt thereof.

5. The method according to claim 4, wherein in the compound of formula (I):

R$^1$ represents alkyl having 1 to 4 carbon atoms which is optionally mono- to trisubstituted by fluorine, represents vinyl, optionally fluorine-substituted cyclopropyl, bicyclo[1.1.1]pent-1-yl, 1.1-dimethylpropargyl, 3-oxetanyl, methylamino, phenyl which is optionally mono- or disubstituted by fluorine, amino or hydroxyl, or represents thiadiazolyl;

R$^2$ represents hydroxyl, optionally ethoxycarbonyl-substituted alkoxy having 1 to 4 carbon atoms, benzyloxy, allyloxy, or propargyloxy;

R$^3$ represents hydrogen, amino, hydroxyl, or fluorine;

A represents N or C—R$^7$ in which

R$^7$ represents hydrogen, halogen, CF$_3$, OCH$_3$, OCHF$_2$, CH$_3$, CN, CH=CH$_2$ or C≡CH or else together with R$^1$ may form a bridge of the structure —*O—CH$_2$—CH—CH$_3$ or —*O—CH$_2$—N—R$^8$ where the atom marked with * is attached to the carbon atom of A and in which R$^8$ is hydrogen or methyl;

B represents N, C—H, C—F, C—Cl, or C—NH$_2$;

Y represents hydrogen or together with R$^2$ may form a bridge of the structure —*S—NH— where the atom marked with * represents Y, and T represents a radical of the formula

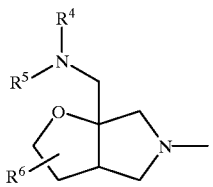

in which

R$^4$ represents H, CH$_3$, C$_2$H$_5$, optionally amino-substituted acyl having 1 to 5 carbon atoms, alkoxycarbonyl, aminocarbonyl, alkylthiothiocarbonyl and dialkoxyphosphoryl having 1 to 4 carbon atoms in the alkyl moiety;

R$^5$ represents H, CH$_3$ or C$_2$H$_5$; and

R$^6$ represents H;

or a pharmaceutically useful hydrate, acid addition salt or alkali metal, alkaline earth metal, silver or guanidinium salt thereof.

6. The method according to claim 4, wherein in the compound of formula (I):

R$^1$ represents alkyl having 1 to 4 carbon atoms which is optionally mono- or disubstituted by fluorine, optionally fluorine-substituted cyclopropyl, phenyl which is optionally mono- or disubstituted cyclopropyl, or phenyl which is optionally mono- or disubstituted by fluorine;

R$^2$ represents hydroxyl, optionally ethoxycarbonyl-substituted alkoxy having 1 to 4 carbon atoms, benzyloxy, allyloxy, or propargyloxy;

R$^3$ represents hydrogen, amino, hydroxyl, or fluorine;

A represents N or C—R$^7$ in which

R$^7$ represents hydrogen, chlorine, fluorine, OCH$_3$, OCHF$_2$, CH$_3$ or CN or else together with R$^1$ may form a bridge of the structure —*O—CH$_2$—CH—CH$_3$, or —*O—CH$_2$—N—CH$_3$ where the atom marked with * is attached to the carbon atom of A;

B represents N, C—H, or C—F;

Y represents hydrogen or together with R$^2$ may form a bridge of the structure —*S—NH— where the atom marked with * represents Y; and T represents a radical of the formula:

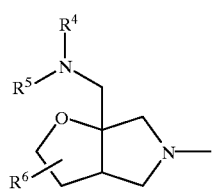

in which

R$^4$ represents H, CH$_3$, C$_2$H$_5$, optionally amino-substituted acyl having 1 to 4 carbon atoms or alkoxycarbonyl having 1 to 4 carbon atoms in the alkyl moiety;

R$^5$ represents H; and

R$^6$ represents H;

or a pharmaceutically useful hydrate, acid addition salt or alkali metal, alkaline earth metal, silver or guanidinium salt thereof.

7. The method according to claim 4, wherein the compound of formula (I) is diastereomerically pure or enantiomerically pure.

8. A method of treating a *Heliobacter pylori* infection or a gastroduodenal disorder associated therewith, said method comprising administering to a patient in need thereof an effective amount therefor of the compound according to claim 2.

* * * * *